(12) United States Patent
Hulot et al.

(10) Patent No.: US 8,354,388 B2
(45) Date of Patent: Jan. 15, 2013

(54) INHIBITORS OF MRP4 FOR THE TREATMENT OF VASCULAR DISORDERS

(75) Inventors: Jean-Sebastien Hulot, Ville d'avray (FR); Anne-Marie Lompre, Egly (FR); Yassine Sassi, Vanves (FR); Philippe Lechat, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 49 days.

(21) Appl. No.: 12/595,122

(22) PCT Filed: Apr. 10, 2008

(86) PCT No.: PCT/EP2008/054361
§ 371 (c)(1), (2), (4) Date: Jul. 20, 2010

(87) PCT Pub. No.: WO2008/122666
PCT Pub. Date: Oct. 16, 2008

(65) Prior Publication Data
US 2010/0278809 A1    Nov. 4, 2010

(30) Foreign Application Priority Data
Apr. 10, 2007 (EP) .................................. 07290433
Dec. 19, 2007 (EP) .................................. 07301710

(51) Int. Cl.
*A61K 48/00* (2006.01)

(52) U.S. Cl. ...... 514/44; 536/24.5; 536/24.1; 536/24.31
(58) Field of Classification Search ............................ None
See application file for complete search history.

(56) References Cited

U.S. PATENT DOCUMENTS
2006/0286041 A1    12/2006   Goeggel et al.
2007/0212366 A1     9/2007   Greinacher et al.

FOREIGN PATENT DOCUMENTS
| WO | 00/24390 | 5/2000 |
|----|----------|--------|
| WO | 00/58471 | 10/2000 |
| WO | 2005/001092 | 1/2005 |
| WO | 2005/044244 | 5/2005 |
| WO | 2006/134022 | 12/2006 |

OTHER PUBLICATIONS van de Water et al. Drug Metabolism and Disposition 2006, vol. 34, No. 8:1393-1397.*
Reid et al. PNAS Aug. 2003, vol. 100; 9244-9249.*
Mitani et al. European Journal of Pharmacology 2003, vol. 466: 223-224.*
Chen et al., J. Biol. Chem., 276(36):33747-33754 (2001).
van de Water et al., Drug Metab. Dispos., 34(8):1393-1397 (2006).

* cited by examiner

*Primary Examiner* — Kimberly Chong
(74) *Attorney, Agent, or Firm* — McAndrews, Held & Malloy Ltd.

(57) ABSTRACT

The invention relates to inhibitors of MRP4 for the treatment and/or the prevention of vascular disorders such as atherosclerosis, post-angioplasty restenosis, pulmonary arterial hypertension or vein-graft disease.

9 Claims, 15 Drawing Sheets a

MRP5

β-actin b c

INHIBITORS OF MRP4 FOR THE TREATMENT OF VASCULAR DISORDERS

Figure 1:
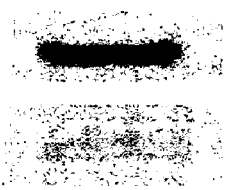
Figure 1:
Figure 1:
Figure 1:
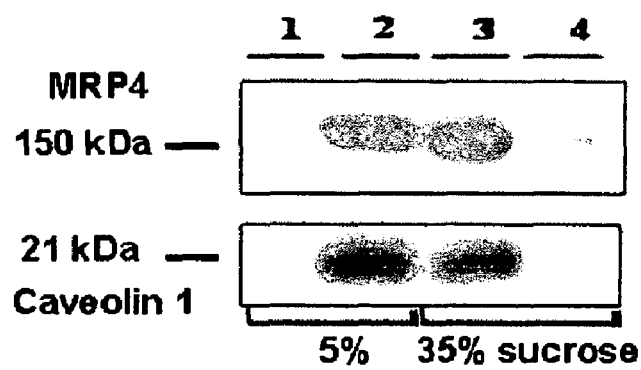

The present application is filed pursuant to 35 U.S.C. 371 as a U.S. National Phase application of International Patent Application No. PCT/EP08/54361, which was filed Apr. 10, 2008, claiming the benefit of priority to European Patent Application No. 07290433.7, which was filed on Apr. 10, 2007, and European Patent Application No. 07301710.5, which was filed on Dec. 19, 2007. The entire text of the aforementioned applications is incorporated herein by reference in its entirety.

FIELD OF THE INVENTION

The invention relates to inhibitors of Multi drug Resistant Protein 4 (MRP4) for the treatment and/or the prevention of vascular disorders such as atherosclerosis, post-angioplasty restenosis, pulmonary arterial hypertension and vein-graft disease.

The present invention relates to gene regulation and cellular physiology in smooth muscle cells. Specifically, the invention relates to the use of inhibitors of MRP4 to block cyclic nucleotides efflux out of cells.

BACKGROUND OF THE INVENTION

Cellular proliferation and growth are two mechanisms leading to vascular remodelling commonly observed in vascular muscular cells in response to diverse pathological stimuli. Excessive smooth muscle cells proliferation is a fundamental process that contributes to the injury response in major arterial vessels. Such process is involved in numerous vascular disorders including atherosclerosis, post-angioplasty restenosis, pulmonary arterial hypertension and vein-graft disease (Dzau V J and al., 2002; Novak K., 1998). Identifying modifiers of vascular smooth muscle cell (VSMC) proliferation is thus a major focus of research in cardiovascular biology and medicine.

Stereotypical pattern of changes in gene expression that include the re-expression of fetal genes are observed. Such differences are controlled by particular underlying signalling pathways. Advances in the description of signalling pathways involved in pathological vascular smooth muscle cells proliferation have pointed on regulatory pathways controlled by cyclic nucleotides. Cyclic nucleotides, namely adenosine 3',5'-monophosphate (cAMP) and cyclic guanosine 3',5'-monophosphate (cGMP), are key second messengers acting as negative regulators of smooth muscle cells proliferation. The synthesis of cyclic AMP or cyclic GMP in cells is catalyzed by the adenylyl or guanylyl cyclase enzymes, respectively (McDonald & Murad, 1996; Sunahara and al., 1996). The elevation of intracellular cAMP and cGMP concentrations by cAMP or cGMP analogues, both independently inhibit rabbit vascular smooth muscle cell proliferation. (Assender J W. and al, 1992). Reexpression of constitutively active Protein kinase G (PKG) (or wild type PKG with cGMP stimulation) inhibits VSMC migration, enhances apoptosis, reduces proliferation, and decreases neointima formation after vascular injury. (Boerth N J and al,. 1997; Sinnaeve P and al. 2002).

Following these results, focus has been made on process involved in cyclic nucleotides elimination. These cyclic nucleotides can be degraded by specific members of the phosphodiesterase (PDE) superfamily that are responsible for the hydrolysis of intracellular cAMP and cGMP. (Rybalkin and al., 2003)

Recently, Chen et al (JBC; 2001) has reported that the cAMP and the cGMP can also be transported by active efflux transporters, namely the multidrug resistance proteins (MRP) MRP4 and MRP5, encoded by the ATP-Binding Cassette transporters class C (ABCC) 4 and ABCC5 genes respectively. Among this transporter family, MRP4 and MRP5 shows high affinity for cAMP and cGMP. To date, however, the physiological function of these proteins remains unclear. Recently, MRP4 and MRP5 were identified as ATP-dependent export pumps for cyclic nucleotides (Jedlitschky and al., 2000; Chen and al., 2001) and it has been shown that MRP4 and MRP5 are expressed in the porcine coronary and pulmonary arteries (Mitani et al; 2003).

SUMMARY OF THE INVENTION

The present invention formally demonstrates for the first time that smooth muscle cells proliferation may be inhibited by inhibiting MRP4.

The invention relates to an inhibitor of MRP4 for inhibiting the growth and proliferation of smooth muscle cells.

The invention relates to an inhibitor of MRP4 for the treatment of a vascular disorder. Examples of vascular disorders which may be treated with MRP4 inhibitors are atherosclerosis, post-angioplasty restenosis, pulmonary arterial hypertension and vein-graft disease.

The invention relates to a method for treating a vascular disorder in a subject comprising administering to the subject a therapeutically effective amount of a pharmaceutical composition comprising an inhibitor of MRP4.

The invention also relates to the use of an inhibitor of MRP4 for the manufacture of a medicament for inhibiting the proliferation of smooth muscle cells.

DETAILED DESCRIPTION OF THE INVENTION

Definitions

The term "MRP4" has its general meaning in the art and refers to the Multidrug Resistance Protein 4. MRP4 is also designated as ABCC4 protein, ATP-binding cassette, subfamily C (CFTR/MRP), member 4, EST 170205, MRP/cMOAT-related ABC transporter (MOAT-B), Multi-specific organic anion transporter-B (MOATB), Multidrug resistance-associated protein 4 in the art. The term may include naturally occurring MRP4s and variants and modified forms thereof. The term may also refer to fusion proteins in which a domain from MRP4 that retains at least one MRP4 activity is fused, for example, to another polypeptide (e.g., a polypeptide tag such as are conventional in the art). The MRP4 can be from any source, but typically is a mammalian (e.g., human and non-human primate) MRP4, particularly a human MRP4. An exemplary native MRP4 amino acid sequence is provided in GenPept database under accession number AAH41560 and an exemplary native nucleotide sequence encoding for MRP4 is provided in GenBank database under accession number NM_005845

The expression "inhibitor of MRP4" should be understood broadly, it encompasses inhibitors of the MRP4 mediated cellular efflux of cyclic nucleotides, hereafter called MRP4 activity, and inhibitors of the expression of MRP4.

An "inhibitor of expression" refers to a natural or synthetic compound that has a biological effect to inhibit or significantly reduce the expression of a gene. Consequently an "inhibitor of MRP4 expression" refers to a natural or synthetic compound that has a biological effect to inhibit or significantly reduce the expression of the gene encoding for the MRP4 gene.

As used herein, the terms "selective inhibitor of MRP4" refer to an inhibitor which is selective for MRP4 as compared with the other Multidrug Resistance Proteins (MRPs) such as MRP1, MRP2, MRP3, MRP5, MRP6, MRP7, MRP8, MRP9, MRP10, MRP11, MRP12 and MRP13. By "selective" it is meant that Ki of the inhibitor for MRP4 is at least 5-fold, preferably 10-fold, more preferably 25-fold, still preferably 100-fold lower than the Ki for other MRPs. The Ki of an inhibitor of MRP4 may be determined using various methods well known in the art.

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

As used herein, the term "subject" denotes a mammal, such as a rodent, a feline, a canine, and a primate. Preferably, a subject according to the invention is a human.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

By "biocompatible" is meant a material which elicits no or minimal negative tissue reaction including e. g. thrombus formation and/or inflammation.

Therapeutic Methods and Uses

The present invention provides methods and compositions (such as pharmaceutical compositions) for inhibiting the proliferation of smooth muscle cells, in particular arterial smooth muscle cells. The present invention also provides methods and compositions (such as pharmaceutical compositions) for treating and/or preventing vascular disorders such as atherosclerosis, post-angioplasty restenosis, pulmonary arterial hypertension and vein-graft disease.

Thus, an object of the invention is an inhibitor of MRP4, preferably selective, for inhibiting the proliferation of smooth muscle cells. The inhibitor of MRP4 may be used for the treatment and/or the prevention of vascular disorders such as atherosclerosis, post-angioplasty restenosis, pulmonary arterial hypertension or vein-graft disease.

In a preferred embodiment the inhibitor of MRP4 is a selective inhibitor of MRP4.

In one embodiment, the MRP4 inhibitor may be a low molecular weight inhibitor, e. g. a small organic molecule. Examples of MRP4 inhibitor are given in US2006/0286041, in Reid et al. (Molecular Pharmacology, 63: 1094-1103, 2003) and in Rémon et al. (J Am Soc Nephrol 13:595-603, 2002).

Small organic MRP4 inhibitors that may be used by the invention include, but are not limited to compounds selected from the group consisting of N-Acetyl-dinitrophenyl-Cysteine, Benzbromarone, Cholate, Diclofenac, Dipyrimadole, Dehydroepiandrosterone 3-glucuronide, Dehydroepiandrosterone 3-sulphate, Dilazep, Dinitrophenyl-5-glutathione, Estradiol 17-[beta]-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycohthocholic acid sulphate, Ibuprofen, Indomethacin, Indoprofen, Ketoprofen, Lithocholic acid sulphate, Methotrexate, MK571 (([pound])-3-[[[3-[2-(7-Chloro-2-quinolyl]ethenyl]phenyl]-[[3-dimethylamino)-3-oxopropyl]thio]methyl]thio]-propanoic acid), [alpha]-Naphthyl-[beta]-D-glucuronide, Nitrobenzyl mercaptopurine [pi]boside, Probenecid, PSC833, Sulfinpyrazone, Taurochenodeoxycholate, Taurocholate, Taurodeoxycholate, Taurohthocholate, Taurolithochohc acid sulphate, Topotecan, Trequinsin, Verapamil and Zap[pi]nast, optionally in the form of the racemates, the enantiomers, the diastereomers and optionally the pharmacologically acceptable acid addition salts and the hydrates thereof.

In a preferred embodiment the inhibitor of MRP4 is not a Phosphodiesterase (PDE) inhibitor selected from the group consisting of PDE3 inhibitors, PDE4 inhibitors, PDE5 inhibitors By acid addition salts of MRP4 inhibitor, with pharmacologically acceptable acids are meant for example salts selected from the group comprising the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hyd rosuccm ate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts, the salts of hydrochloric acid, methanesulphonic acid, benzoic acid and acetic acid are particularly preferred according to the invention In another embodiment the MRP4 inhibitor is an antibody or antibody fragment that can partially or completely block the MRP4 transport activity (i. e. a partial or complete MRP4 blocking antibody or antibody fragment).

In particular, the MRP4 inhibitor may consist in an antibody directed against the MRP4, in such a way that said antibody blocks the activity of MRP4.

Antibodies directed against the MRP4 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against MRP4 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-MRP4, single chain antibodies. MRP4 inhibitors useful in practicing the present invention also include anti-MRP4 fragments including but not limited to $F(ab')_2$ fragments, which can be generated by pepsin digestion of an intact antibody molecule, and Fab fragments, which can be generated by reducing the disulfide bridges of the $F(ab')_2$ fragments.

Alternatively, Fab and/or scFv expression libraries can be constructed to allow rapid identification of fragments having the desired specificity to MRP4.

Humanized anti-MRP4 antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, the inhibitor of MRP4 is an aptamer.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Another aspect of the invention relates to selective inhibitor of MRP4 expression.

MRPs sequences showing low sequence identity (<60%) the inhibitors of MRP4 expression which may be used according to the invention advantageously provides selective inhibition of MRP4 expression, by comparison with other MRPs expression.

Inhibitors of MRP4 expression for use in the present invention may be based on anti-sense oligonucleotide constructs. Anti-sense oligonucleotides, including anti-sense RNA molecules and anti-sense DNA molecules, would act to directly block the translation of MRP4 mRNA by binding thereto and thus preventing protein translation or increasing mRNA degradation, thus decreasing the level of MRP4s, and thus activity, in a cell. For example, antisense oligonucleotides of at least about 15 bases and complementary to unique regions of the mRNA transcript sequence encoding MRP4 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of MRP4 expression for use in the present invention. MRP4 expression can be reduced by contacting a subject or cell with a small double stranded RNA (dsRNA), or a vector or construct causing the production of a small double stranded RNA, such that MRP4 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). A siRNA efficiently silencing MRP4 has been developed. This siRNA will target the several MRP4 splicing variants (NM_005845, BC041560, AY081219,AF541977,AY133680,AY133679, AY133678). The sense sequence is 5'-CAGUGUUCUUA-CACUUCCUTT-3' (SEQ ID NO:7) and anti-sense: 5'-AG-GAAGUGUAAGAACACUGTT-3' (SEQ ID NO:8).

shRNAs (short hairpin RNA) can also function as inhibitors of MRP4 expression for use in the present invention. An example of short hairpin RNA according to the invention is a shRNA comprising the sequence as set forth in SEQ ID NO: 9: GCAAATGTGGATCCGAGAA.

Ribozymes can also function as inhibitors of MRP4 expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of MRP4 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of MRP4 expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing MRP4. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter can be, e.g., a smooth muscle specific promoter, such as a smooth muscle alpha actin promoter, SM22α promoter. The promoter can also be, e.g., a viral promoter, such as CMV promoter or any synthetic promoters.

The selective inhibitor of MRP4 activity and/or expression may be administered in the form of a pharmaceutical composition, as defined below.

Preferably, said inhibitor is administered in a therapeutically effective amount.

By a "therapeutically effective amount" is meant a sufficient amount of the MRP4 inhibitor to treat and/or to prevent vascular disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Inhibitors of the invention can be further identified by screening methods described in the state of the art. The screening methods of the invention can be carried out according to known methods.

The screening method may measure the binding of a candidate compound to MRP4, or to cells or membranes bearing MRP4, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., inhibitor or substrate).

For example, MRP4 cDNA may be inserted into an expression vector that contains necessary elements for the transcription and translation of the inserted coding sequence. Following vector/host systems may be utilized such as Baculovirus/Sf9 Insect Cells Retrovirus/Mammalian cell lines like HepB3, LLC-PK1, MDCKII, CHO, HEK293 Expression vector/Mammalian cell lines like HepB3, LLC-PK1, MDCKII, CHO, HEK293. Such vectors may be then used to transfect cells so that said cells express recombinant MRP4 at their membrane. It is also possible to use cell lines expressing endogenous MRP4 protein (THP-1, U937, WI-38, WI-38 (VA-13 subline), IMR-90, HEK-293).

Cells obtained as above described may be the pre-incubated with test compounds and subsequently stimulated with compounds known to elevate cellular cAMP and/or cGMP production (such as Forskolin, Isoprenaline,for cAMP and SNP for cGMP). Test compounds are screened for their ability to enhance intracellular cAMP and/or cGMP levels and reduce extracellular cAMP and/or cGMP levels.

In a further embodiment, membrane vesicles may be prepared from cell lines obtained as above described. Membrane vesicles may be then pre-incubated with test compounds. Subsequently, cAMP, ATP, and ATP regeneration systems (creatine kinase and creatine phosphate) are added to the membrane vesicles, and compounds are screened for their ability to inhibit the accumulation of cAMP inside the membrane vesicles.

Pharmaceutical Compositions

A further object of the invention relates to a pharmaceutical composition for treating and/or preventing vascular disorders such as atherosclerosis, post-angioplasty restenosis, pulmonary arterial hypertension or vein-graft disease, wherein said composition comprises a selective inhibitor of MRP4 expression and/or activity The MRP4 inhibitor may be combined with a pharmaceutically acceptable excipient, and optionally a sustained-release matrix, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The MRP4 inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCI solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The MRP4 inhibitor of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations ; time release capsules ; and any other form currently used.

Pharmaceutical compositions of the invention may include any further agent which has the capacity of limiting the cyclic nucleotides (cGMP cAMP) elimination. Such agents may include but are not limited to specific phosphodiesterase (PDE) superfamily inhibitors including PDE3, PDE4 and PDE5 inhibitors. Examples of PDE4 inhibitors include rolipram and those described in patent documents US2005234238 DE10156229, DE10135009 and WO0146151. Examples of PDE5 inhibitors include sildenafil, vardenafil and tadalafil. Particularly preferred are PDE5 inhibitors that are marketed, e.g. VIAGRA® which is sildenafil citrate and which can be administered in this form. Other examples of PDE5 inhibitors also include those described in paten documents WO2005012303 and US2006106039.

Pharmaceutical compositions of the inventions may include any other anti-proliferative agent that reduce smooth muscle cell proliferation. For example, the anti-proliferative agent may be rapamycin, rapamycin derivatives, paclitaxel, docetaxel, 40-0-(3-hydroxy)propyl-rapamycin, 40-O-[2-(2-hydroxy)ethoxy]ethyl-rapamycin, and 40-O-tetrazole-rapamycin, ABT-578, everolimus and combinations thereof.

Pharmaceutical compositions of the invention may include compounds selected from the group consisting of antibodies, receptor ligands, enzymes, adhesion peptides, oligosaccharides, oligonucleotides and the like. Such compounds may be blood clotting factors, inhibitors or clot dissolving agents such as streptokinase and tissue plasminogen activator. Such agents can also include a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. Such compounds can also fall under the genus of antineoplastic, cytostatic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N. J.), and mitomycin (e.g. Mutamycin® from Bristol-Myers Squibb Co., Stamford, Conn.). Examples of such antiplatelets, anticoagulants, antifibrin, and antitlirombins include heparinoids, hirudin, recombinant hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, and thrombin inhibitors such as Angiomax® (Biogen, Inc., Cambridge, Mass.). Examples of cytostatic agents include angiopeptin, angiotensin converting enzyme inhibitors such as captopril (e.g. Capoten and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof. Synonyms of actinomycin D include dactinomycin, actinomycin IV, actinomycin I1, actinomycin X1, and actinomycin Ci. Other compounds include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, anti-inflammatory agents, antivirals, anticancer drugs, anticoagulant agents, free radical scavengers, steroidal anti-inflammatory agents, non-steroidal anti-inflammatory agents, antibiotics, nitric oxide donors, super oxide dismutases, super oxide dismutases mimics, 4-amino- 2,2,6,6-tetramethylpiperidine-1-oxyl (4-amino-TEMPO), dexamethasone, clobetasol, aspirin, prodrugs thereof, co-drugs thereof, and a combination thereof. The foregoing substances are listed by way of example and are not meant to be limiting. Other active agents which are currently available or that may be developed in the future are equally applicable.

The present invention also relates to a kit for treating a vascular disorder comprising a first pharmaceutical composition comprising an inhibitor of MRP4 and a second pharmaceutical composition comprising one or more Phosphodiesterase (PDE) inhibitors selected from the group consisting of PDE3 inhibitors, PDE4 inhibitors, PDE5 inhibitors and mixtures thereof.

Biomaterials

The present invention also relates to the use of a inhibitor of MRP4 for the preparation of biomaterials or medical delivery devices selected among endovascular prostheses, such as stents, bypass grafts, internal patches around the vascular tube, external patches around the vascular tube, vascular cuff, and angioplasty catheter.

In this respect, the invention relates more particularly to biomaterials or medical delivery devices as mentioned above, coated with such inhibitor of MRP4 expression and/or activity as defined above, said biomaterials or medical devices being selected among endovascular prostheses, such as stents, bypass grafts, internal patches around the vascular tube, external patches around the vascular tube, vascular cuff, and angioplasty catheter. Such a local biomaterial or medical delivery device can be used to reduce stenosis or restenosis as an adjunct to revascularization, bypass or grafting procedures performed in any vascular location including coronary arteries, carotid arteries, renal arteries, peripheral arteries, cerebral arteries or any other arterial or venous location, to reduce anastomic stenosis such as in the case of arterial-venous dialysis access with or without polytetrafluoro-ethylene grafting and with or without stenting, or in conjunction with any other heart or transplantation procedures, or congenital vascular interventions.

For illustration purpose, such endovascular prostheses and methods for coating selective inhibitor thereto are more particularly described in WO2005094916, or are those currently used in the art. The compounds used for the coating of the prostheses should preferentially permit a controlled release of said inhibitor. Said compounds could be polymers (such as sutures, polycarbonate, Hydron, and Elvax), biopolymers/biomatrices (such as alginate,fucans, collagen-based matrices, heparan sulfate) or synthetic compounds such as synthetic heparan sulfate-like molecules or combinations thereof (Davies, et al., 1997; Desgranges, et al., 2001; Dixit, et al., 2001; Ishihara, et al., 2001; Letourneur, et al., 2002; Tanihara, et al., 2001; Tassiopoulos and Greisler, 2000). Other xamples of polymeric materials may include biocompatible degradable materials, e. g. lactone-based polyesters orcopolyesters, e. g. polylactide; polylactide-glycolide; polycaprolactone-glycolide; polyorthoesters; polyanhydrides; polyaminoacids; polysaccharides; polyphospha-zenes; poly(ether-ester) copolymers, e. g. PEO-PLLA, or mixtures thereof; and biocompatible non-degrading materials, e. g. polydimethylsiloxane; poly(ethylene-vinylacetate); acrylate based polymers or coplymers, e. g. polybutylmethacrylate, poly(hydroxyethyl methyl-methacrylate); polyvinyl pyrrolidinone; fluorinated polymers such as polytetrafluoethylene; cellulose esters. When a polymeric matrix is used, it may comprise 2 layers, e. g. a base layer in which said inhibitor is incorporated, such as ethylene-co-vinylacetate and polybutylmethacrylate, and a top coat, such as polybutylmethacrylate, which acts as a diffusion-control of said inhibitor. Alternatively, said inhibitor may be comprised in the base layer and the adjunct may be incorporated in the outlayer, or vice versa.

Such biomaterial or medical delivery device may be biodegradable or may be made of met al or alloy, e. g. Ni and Ti, or another stable substance when intented for permanent use. The inhibitor of the invention may also be entrapped into the met al of the stent or graft body which has been modified to contain micropores or channels. Also internal patches around the vascular tube, external patches around the vascular tube, or vascular cuff made of polymer or other biocompatible materials as disclosed above that contain the inhibitor of the invention may also be used for local delivery.

Said biomaterial or medical delivery device allow the inhibitor releasing from said biomaterial or medical delivery device over time and entering the surrounding tissue. Said releasing may occur during 1 month to 1 year. The local delivery according to the present invention allows for high concentration of the inhibitor of the invention at the disease site with low concentration of circulating compound. The amount of said inhibitor used for such local delivery applications will vary depending on the compounds used, the condition to be treated and the desired effect. For purposes of the invention, a therapeutically effective amount will be administered.

The local administration of said biomaterial or medical delivery device preferably takes place at or near the vascular lesions sites. The administration may be by one or more of the following routes: via catheter or other intravascular delivery system,intranasally, intrabronchially, interperitoneally or eosophagal. Stents are commonly used as a tubular structure left inside the lumen of a duct to relieve an obstruction. They may be inserted into the duct lumen in a non-expanded form and are then expanded autonomously (self-expanding stents) or with the aid of a second device in situ, e. g. a catheter-mounted angioplasty balloon which is inflated within thestenosed vessel or body passageway in order to shear and disrupt the obstructions associated with the wall components of the vessel and to obtain an enlarged lumen.

The biomaterial of the invention may be coated with any other compounds as above described for pharmaceutical compositions, including PDE3, PD4 and/or PDE5 inhibitors.

The invention will further be illustrated in view of the following figures and examples.

FIGURES

FIG. 1: Expression of MRP4 in human coronary artery smooth muscle cells (hCASMC). (a) Representative RT-PCR showing detection of MRP4 and β-actin mRNA in cultured hCASMC (b) Immunofluorescence analysis of MRP4 expression in MRP4 cDNA transfected hCASMC using a polyclonal affinity-purified antibody against MRP4 (c) Western-blot analysis of MRP4 and caveolin 1 expression in hCASMC membranes purified on a discontinuous sucrose gradient showing that MRP4 is present in caveolin1-enriched fractions.

Figure 2:
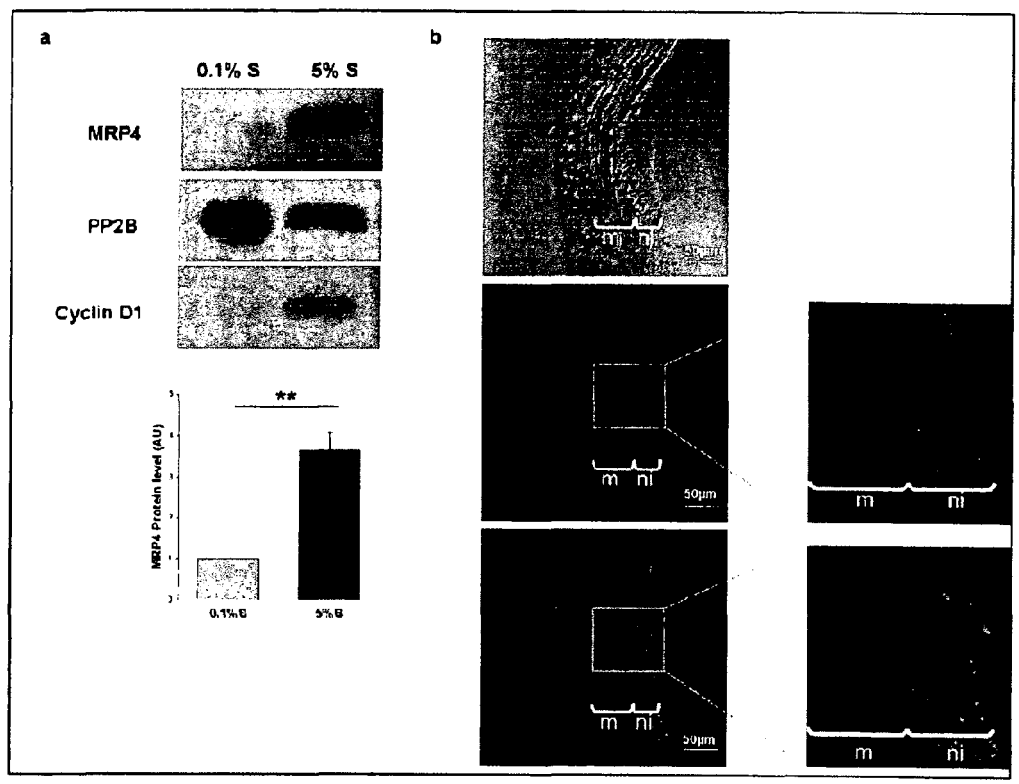

FIG. 2: Upregulation of MRP4 in vitro and in vivo in proliferating smooth muscle cells.(a) MRP4 expression was quantified by western blotting in cultured hCASMC exposed for 72 hours to 5% or 0.1% S. PP2B (Calcineurin) is used as a standard and cyclin D1 as a marker of proliferation. (**: $p<0.01$). (b) Representative sections of balloon-injured rat carotid arteries at d14 after injury. Immunostaining revelead a preponderant expression of MRP4 in the neointima (ni) compared to the media (m). Expression of MRP4 (red) correlated with that of NM-B (green), a phenotype marker of the smooth muscle cell proliferation.

Figure 3:
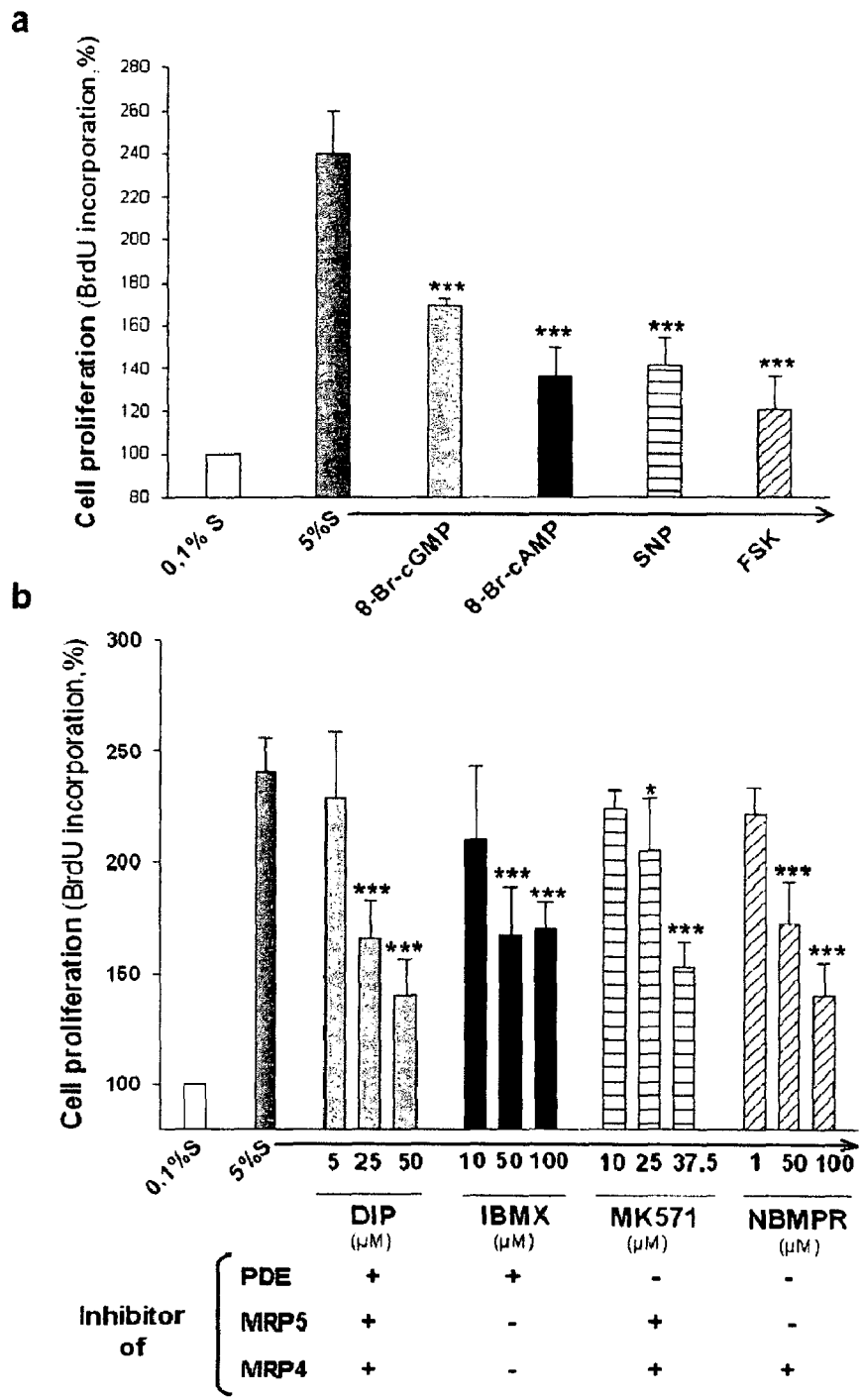

FIG. 3: Antiproliferative effects of cAMP and cGMP and MRP inhibitors in hCASMC. Cell proliferation was measured 72 hours after plating by BrdU incorporation and expressed as relative increase compared to growth supplement starved (0.1% S) cells. (a) Cell proliferation in presence of permeant cyclic nucleotides 8-Br-cAMP (100 μM) and 8-Br-cGMP (200 μM), SNP (a NO donor, 1 mM) and Forskolin (FSK, a stimulator of adenylate-cyclase activity, 5 μM).

n=3 experiments in triplicate. (b) Dose-effect of MRP and PDE inhibitors (DIP: Dipyridamole, IBMX, MK571 and NBMPR) on hCASMC proliferation. n=3 experiments in triplicate. * p≦0.05,  p≦0.01, * p≦0.001

Figure 4:
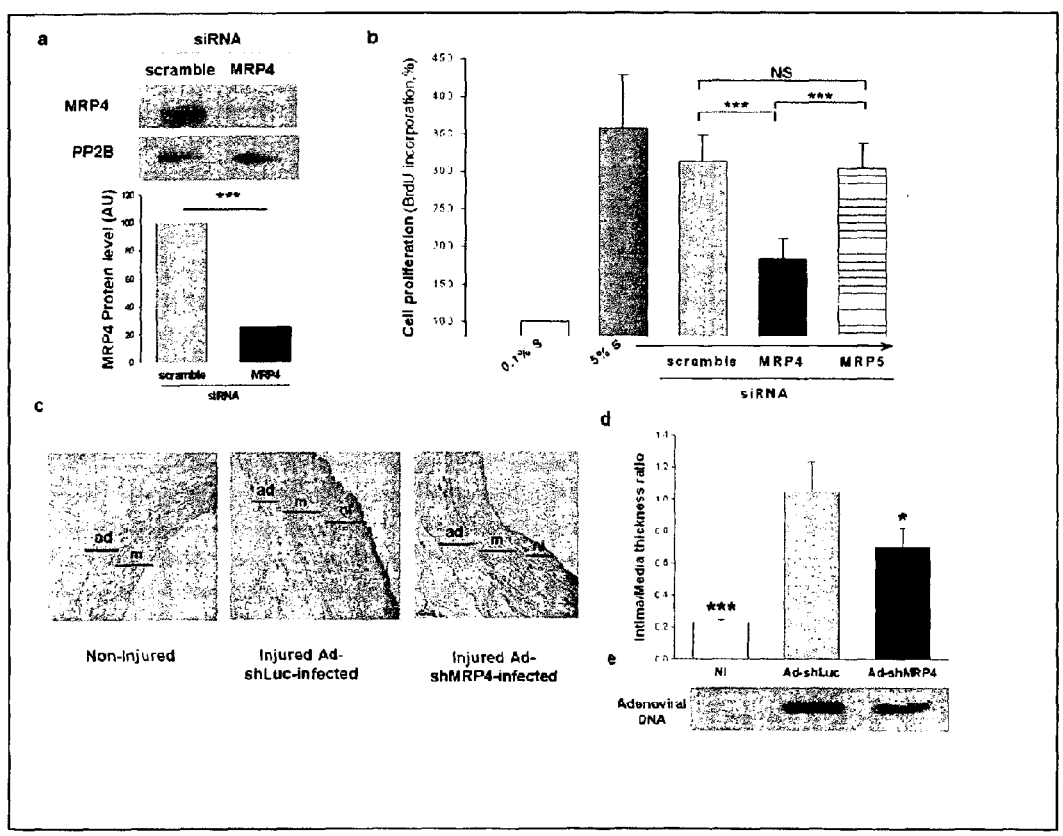

FIG. 4: Inhibition of hCASMC proliferation using MRP4 siRNA: (a) Western-Blot analysis of total cells lysates from hCASMC transfected for 72 h with MRP4 siRNA or scramble siRNA showing efficient silencing of MRP4. Proteins were incubated with anti-MRP4 antibody or anti-PP2B (Calcineurin) antibodies. Calcineurin is used as a control of loading. n=3; P≦0.001 (b) Effect of MRP4 and MRP5 siRNAs on hCASMCs proliferation (assessed by BrdU incorporation) compared to scramble siRNA. n=5 experiments in triplicate; *** p≦0.001 for MRP4 compared to scramble or MRP5. (c) Representative hematoxylin-eosin staining of non-injured (NI) and injured carotid arteries, 14 days after surgery. (d) Average data of intima/media thickness ratio of the above 3 groups (*p<0.05, ***p<0.001 compared with Ad-shLuc infected). m indicates media; ni, neointima; ad, adventitia. (n=5 for non-injured carotid, n=4 for Ad-shLuc infected and n=6 for Ad-shMRP4 infected). (e) PCR on carotid arteries: DNA from rat carotids was extracted and adenovirus expression was assayed by PCR.

Figure 5:
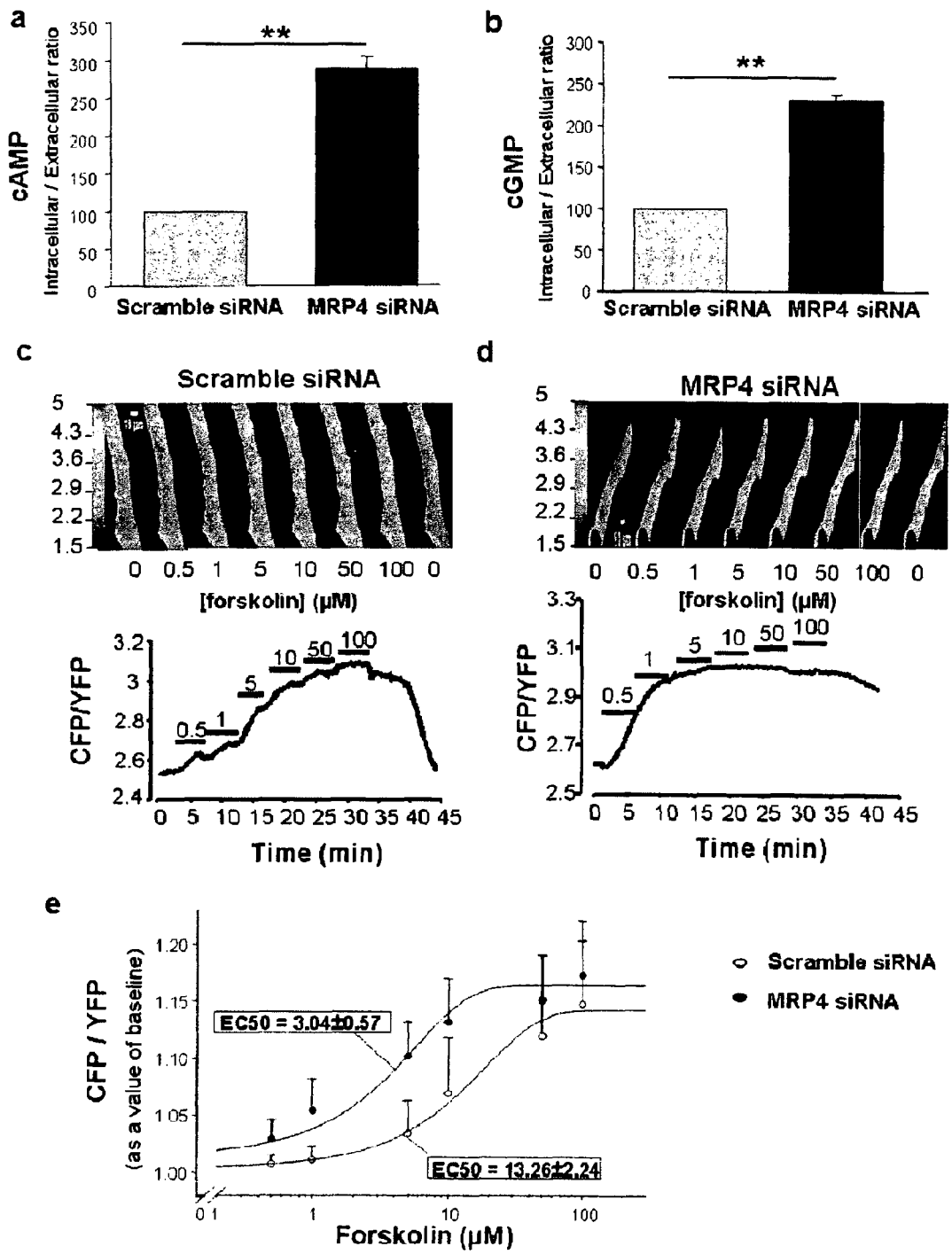

FIG. 5: Effect of MRP4 siRNA on cAMP and cGMP cellular levels: Intracellular/extracellular ratio levels of (a) cAMP or (b) cGMP on hCASMCs transfected with MRP4 or scramble siRNA for 72 h and measured by specific competitive enzyme immunoassay(** p<0.01; n=3). (c, d) Effect of forskolin superfused at increasing concentrations (from 0.5 µM to 100 µM) on intracellular cAMP measured by the FRET-based sensor Epac2-camps in two representative hCASMC transfected with either scramble (c) or MRP4 (d) siRNAs. Raw images obtained upon CFP excitation at 440±20 nm in both cells and time course of the corresponding cell-averaged corrected CFPNFP ratio are reported. CFP and YFP fluorescence indicated that Epac2-camps localizes mainly in the cytosol in both cells. In the scramble siRNA transfected cell (c), application of 5 µM forskolin provided a cAMP rise reflected by the increase in the basal CFP/YFP ratio. In the MRP4 siRNA transfected cell (d) forskolin concentration as low as 0.5 µM already resulted in a significant cAMP increase. (e) Concentraction-response curve (logarithmic scale) of FRET measurements in hCASMCs transfected with MRP4 siRNA (n=11) or scramble siRNA (n=12) and transiently transfected with Epac2-camps. Basal CFP/YFP ratio was similar in both groups of cells. Continuous lines are fit of the data points according to the Hill equation (see Methods). MRP4 RNA interference in hCASMC resulted in a leftward shift of the concentration-response curve to forskolin, as indicated by the significantly different $EC_{50}$ values obtained for the drug in the two groups of experiments.

Figure 6:
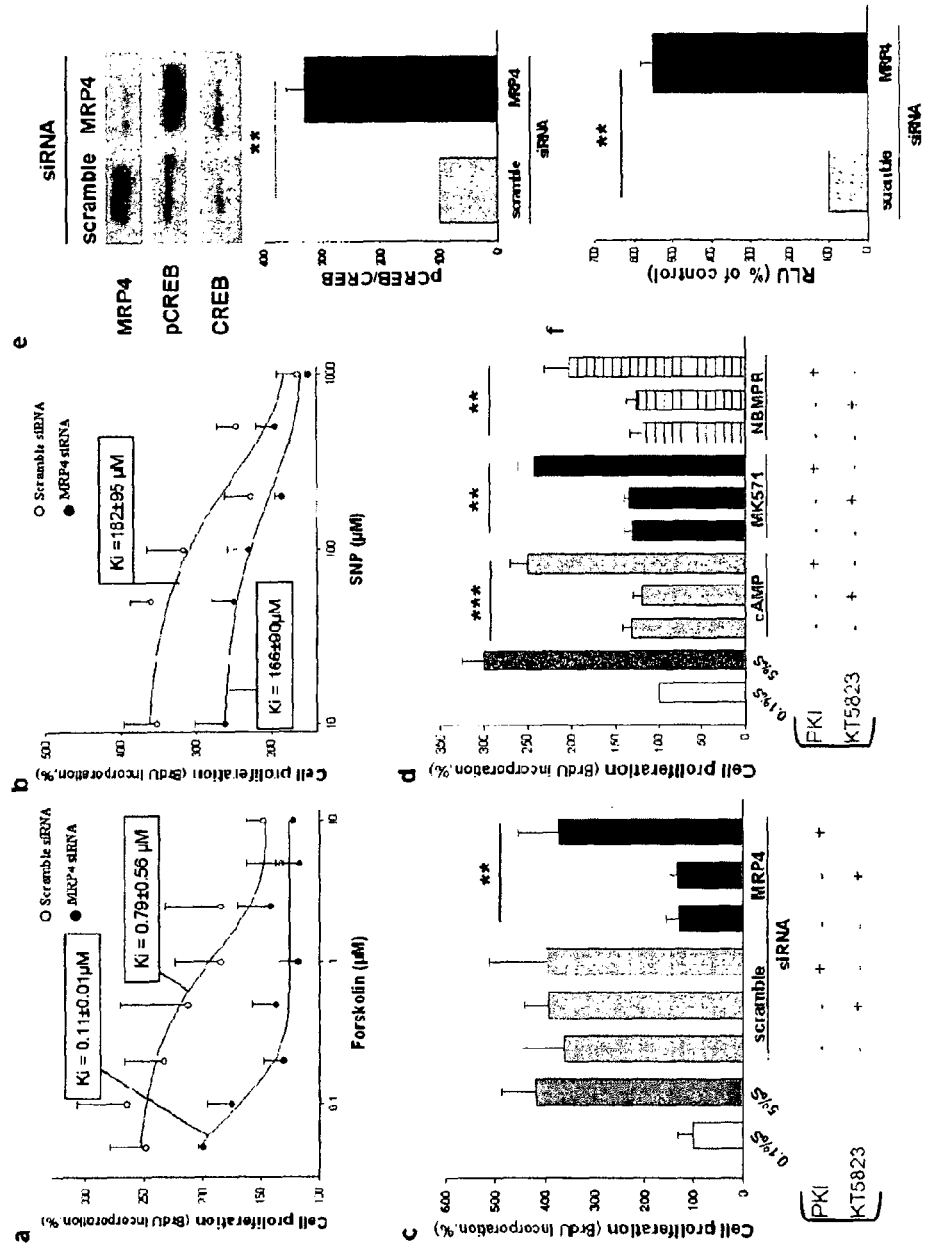

FIG. 6: MRP4 inhibition may enhance the cAMP but not cGMP effect on hCASMC proliferation. Dose-dependent anti-proliferative effect in cells transfected for 72 hours with MRP4 or scramble siRNA.of (a), the activator of cAMP signalling forskolin, or (b) the activator of cGMP signalling SNP (n=5) (c,d) Evaluation of hCASMC proliferation in cells transfected with MRP4 or scramble siRNA (c) or treated with the MRP inhibitors NMBPR (100 µM) and MK571 (37.5 µM) (d) in presence of specific inhibitors of PKA or PKG. A reversal of the effect of MRP4 inhibition on hCASMC proliferation in presence of Ad-PKI (a specific PKA inhibitor) but not KT5823 (a specific PKG inhibitor) was observed in both cases. n=3 per group,  p≦0.01, * p≦0.001. (e) Representative western blot and quantitative evaluation of phosphorylated CREB (pCREB) in proliferating hCASMC transfected with MRP4 or scramble siRNA (n=3, ** p<0.01).

(f) Quantitative evaluation of the activity of the cAMP responsive element CRE measured by the luciferase reporter CRE-Luc in proliferating hCASMC transfected with scramble or MRP4 siRNA. (n=3, ** p<0.01)

Figure 7:
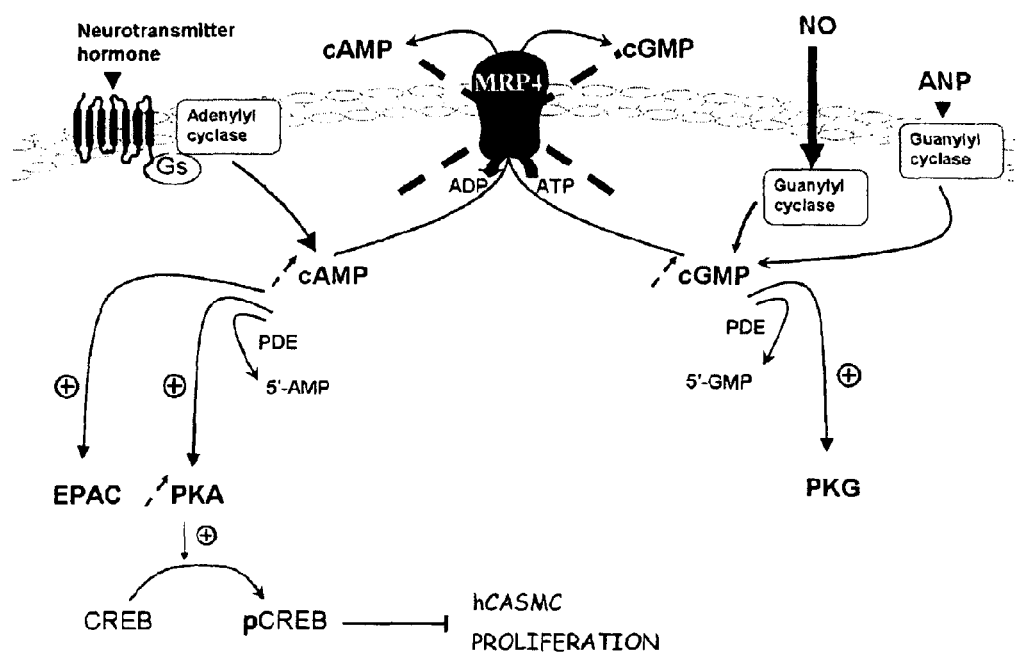

FIG. 7: Representative scheme of MRP4 involvement in the anti-proliferative effect on smooth muscle cells of cyclic nucleotide.

Figure 8:
Figure 8:
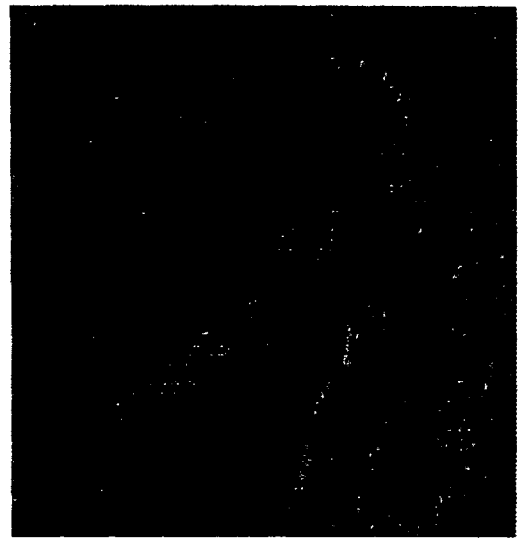
Figure 8:
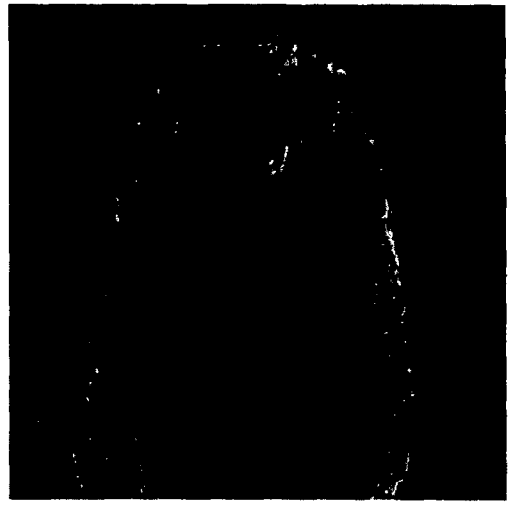

FIG. 8. MRP4 staining in lung tissue. Immunofluorescence analysis of MRP4 expression in human pulmonary arteries. (A) Immunostaining in a normal pulmonary artery reveals an MRP4 expression (red) in the media (green: autofluorescence). (B&C) In pathological pulmonary arteries (from two patients with pulmonary hypertension), immunostaining shows that MRP4 is expressed in the media and in the neo-intima (B) or in the hypertrophic media (C).

Figure 9:
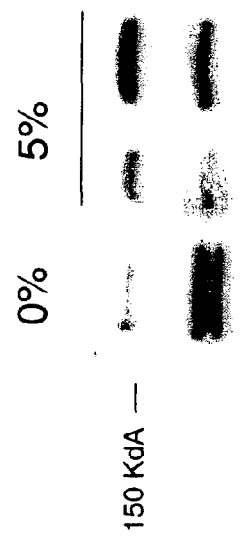

FIG. 9. MRP4 expression in isolated smooth muscle cells from human pulmonary arteries. Western blot analysis in cultured smooth muscle cells exposed for 72 h to 0% S or 5% S showing a basal expression which increases in proliferative conditions.

Figure 10:
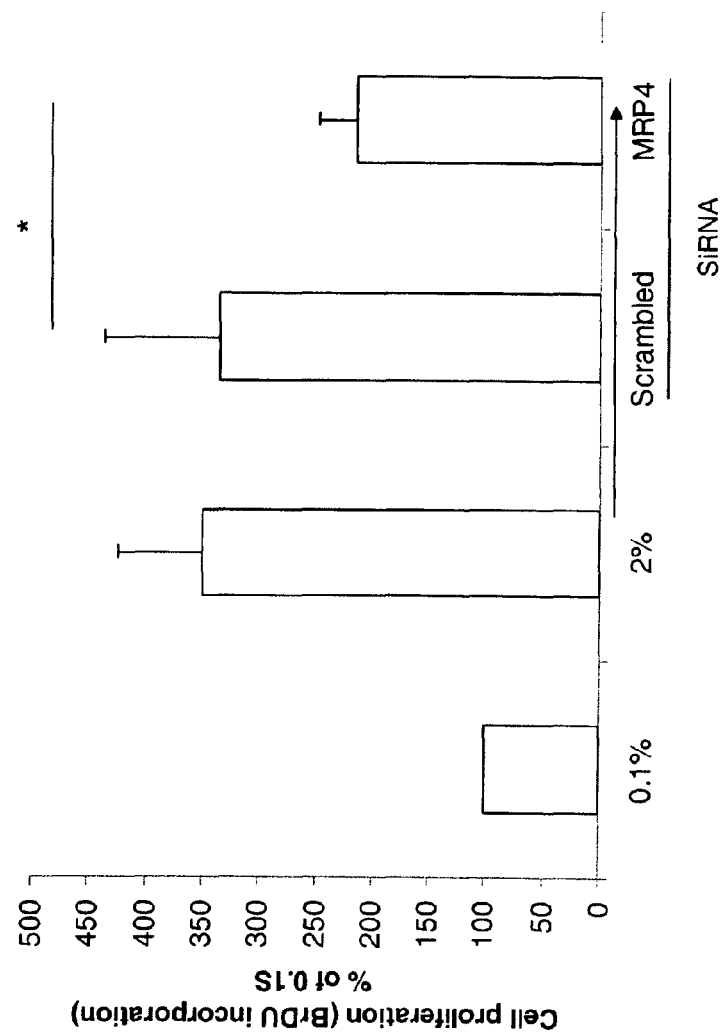

FIG. 10. Inhibition of hPASMC (human pulmonary artery smooth musclulare cells) proliferation with MRP4 siRNA. Effect of MRP4 siRNA on cell proliferation (assessed by BrDU incorporation) compared to scrambled siRNA showing a significant decrease.

Figure 11:
Figure 11:
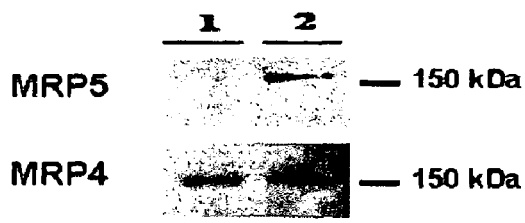
Figure 11:

FIG. 11: Expression of MRP5 and MRP4 in hCASMC. (a) Detection of MRP5 and β-actin mRNA in hCASMC using RT-PCR. (b) Western blot analysis of MRP4 and MRP5 expression in total (1) and membrane (2) lysates (c) Immunofluorescence detection of MRP5 in human coronary artery showing predominant expression in the endothelial layer.

Figure 12:
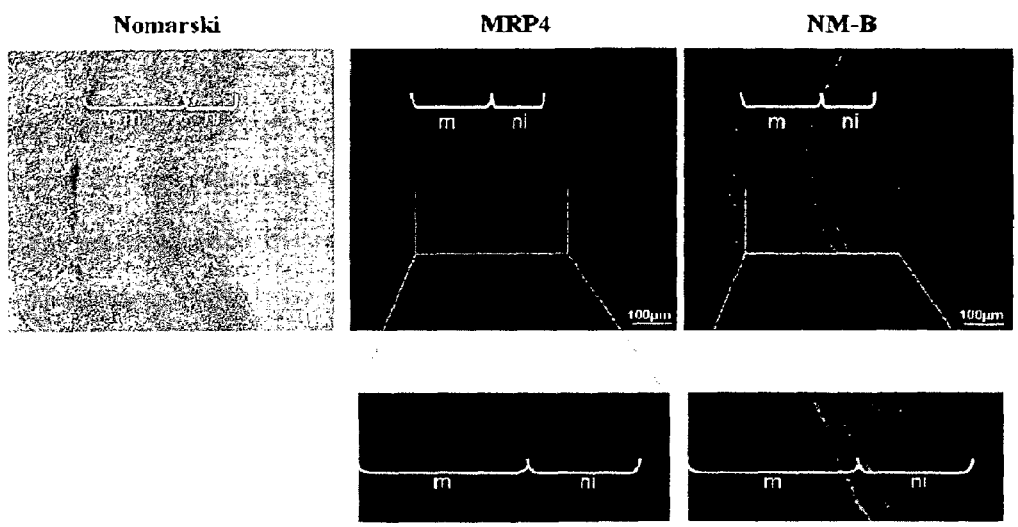

FIG. 12: Expression of MRP4 in human coronary artery. Representative section of an explanted human coronary artery from ischemic cardiomyopathy stained with MRP4 and NM-B, a marker of the smooth muscle cells synthetic/proliferative phenotype.

Figure 13:
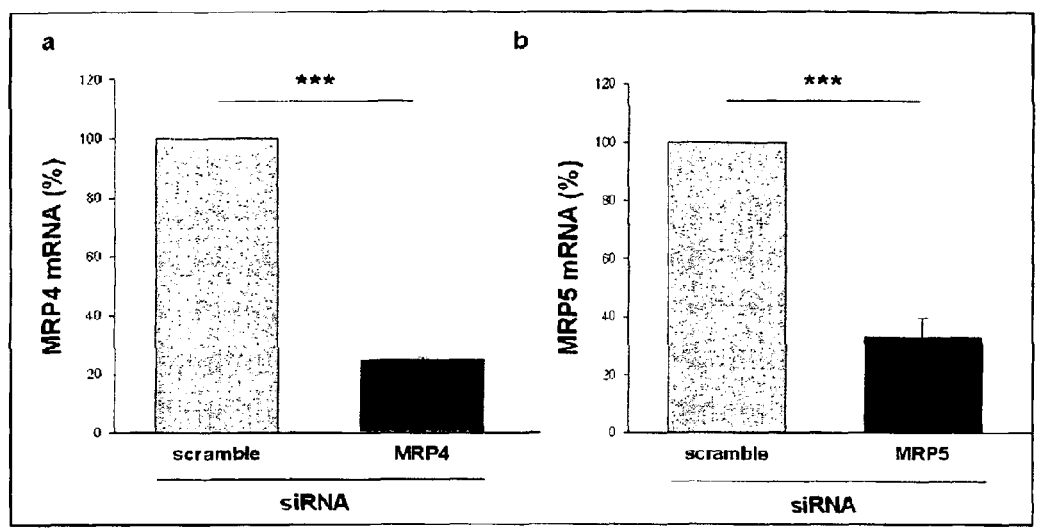

FIG. 13: Evaluation of siRNA silencing efficiency. Quantitative real-time PCR with gene specific primers of MRP4 (a) or MRP5 (b) on hCASMC transfected during 72 h with MRP4, MRP5 or scramble siRNA (n=3, *** p<0.001).

Figure 14:
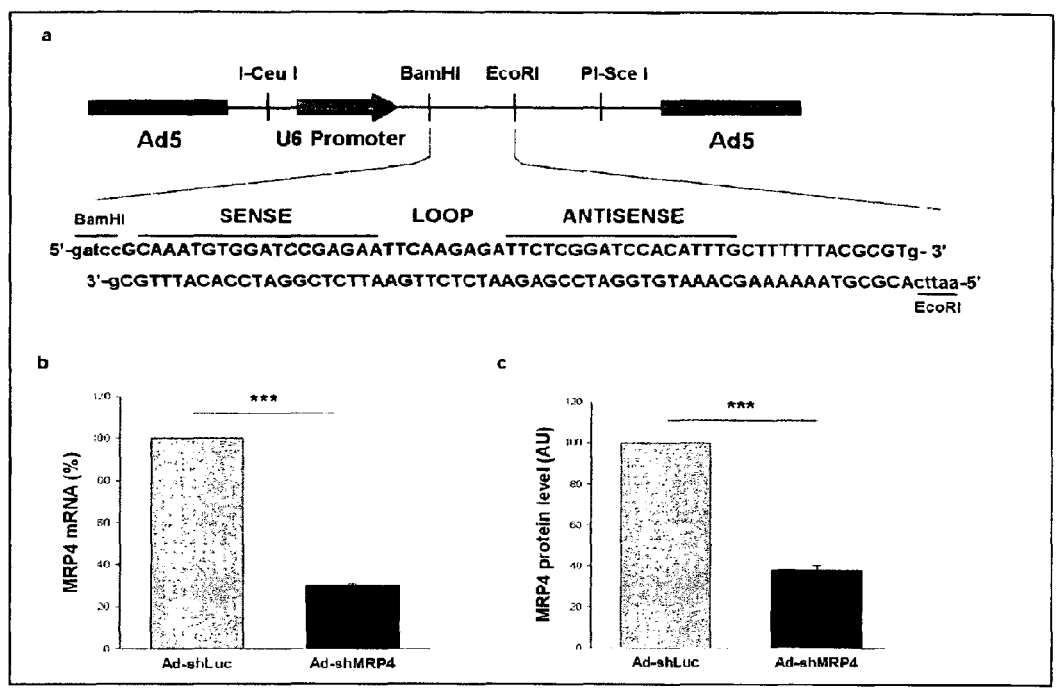

FIG. 14. Adenovirus shRNA MRP4: (a) Map of Ad-shMRP4 vector and MRP4 shRNA sequence (SEQ ID NO: 14 and 15) (b,c) Quantitative real-time PCR (b) and western blot (c) on rat smooth muscle cell transfected during 72 h with Ad-shMRP4 or Ad-shLuc (n=3, *** p<0.001). Viruses were used at a multiplicity of infection (MOI) of 30.

Figure 15:
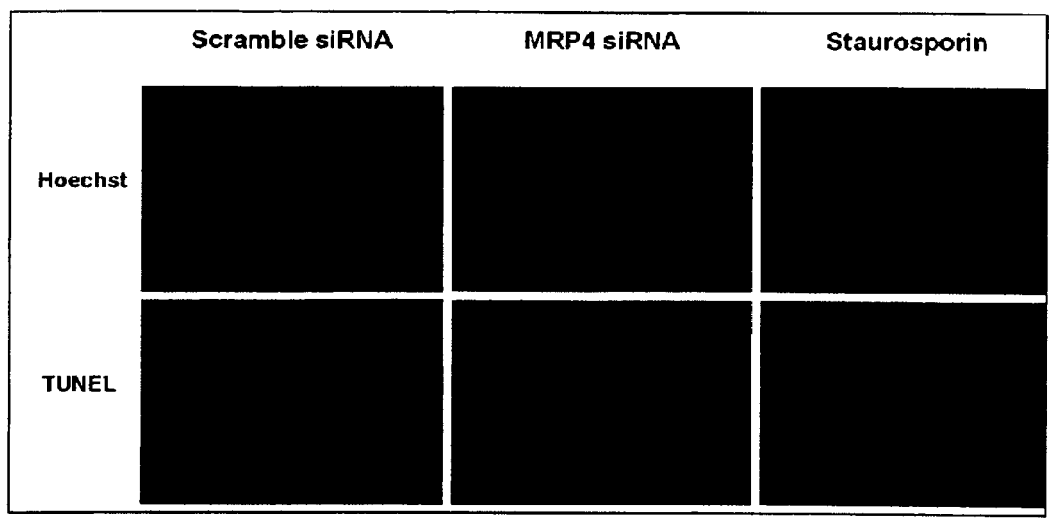

FIG. 15: MRP4 silencing is not associated with apoptosis in hCASMC. MRP4 or scramble siRNA were transfected in hCASMC for 72 h and the apoptosis was analyzed by TUNEL staining (ApopTag Red, Serologicals Corp). For the positive control, cells were treated with staurosporin (10 µM) for 1 h.

EXAMPLE

Abstract

Cyclic nucleotides are degraded by specific phosphodiesterases and are postulated to be eliminated by active efflux transporters, namely the multidrug resistance proteins, MRP4 and MRP5. To study the role of MRP4/5 in cell signalling we used, as a model, arterial smooth muscle cells. MRP4 but not MRP5 was shown to be up-regulated during proliferation of arterial smooth muscle cells in vivo and in vitro. Inhibition of MRP4 resulted in a significant increase in intracellular cAMP and cGMP levels and was sufficient to block proliferation and to prevent neointimal growth in injured-rat carotid arteries. The anti-proliferative effect of MRP4 inhibition is related to the activation of the PKA/CREB pathway. We provide first evidences that MRP4 acts as an independent endogenous regulator of intra-cellular cyclic nucleotide levels and identified inhibition of MRP4 as a new way to prevent vascular smooth muscle proliferative diseases.

Introduction

Cyclic adenosine monophosphate (cAMP) and cyclic guanosine monophosphate (cGMP) are second messengers that relay external signals to downstream key effector proteins. The most common targets are cAMP-dependent protein kinase (PKA) and the cGMP-dependent protein kinase (PKG) which regulate a large number of processes by phosphorylating target proteins but cAMP and cGMP also exert their function by binding certain ion channels[1] and exchange proteins[2]. The signalling events in response to extracellular stimulation arise from an ingenious regulation of intracellular cyclic nucleotide levels which result from a balance between their production and their elimination. Classically, cyclic nucleotide elimination has been linked to hydrolysis mediated by cyclic nucleotide phosphodiesterases (PDEs). PDEs constitute a large superfamily of enzymes encoded by several genes with tissue-specific expression of a large number of splice variants[3]. In several models including vascular smooth muscle cells, PDEs have been shown to regulate the amplitude and duration of intracellular cyclic nucleotide signalling[4]. For instance, Sildenafil, a selective PDE5 inhibitor used to treat human erectile dysfunction via raising cGMP availability, deactivates multiple signalling pathways associated with cardiac hypertrophy[5] (the calcineurin/NFAT, PI3K/Akt and ERK1/2 signalling pathways) and proliferation of vascular smooth muscle cells with some therapeutic success in the treatment of pulmonary arterial hypertension[5,6]. However, the lack of isoform- or variant-specific inhibitors and the compartmentation of cyclic nucleotide signalling[4] represent additional levels of complexity to achieve selective therapeutic effects. Moreover, it is poorly understood whether PDEs may represent the unique regulator of cyclic nucleotide pathways.

The multidrug resistance associated-protein MRP4 (ABCC4), a member of a large family of transmembrane proteins (ATP-Binding Cassette transporters family class C) involved in the active transport of substrates out of cells, was found to actively efflux nucleoside monophosphate analogs from mammalian cells[7]. MRP4 and MRP5 (ABCC5), another member of the ABCC family, were then shown to function as energy-dependent transporters for cAMP and cGMP[8,9]. MRP4 and MRP5 expression has been reported in several tissues including smooth muscle cells[10-12], but their physiological function remains unclear. Especially, whether the direct elimination of cyclic nucleotides by these transporters may be an additional or alternative mechanism acting upstream of cyclic nucleotide catabolism was not yet known.

To delineate the MRP4/5 function in cyclic nucleotide-dependent biological processes, we used arterial smooth muscle cells as increase in cyclic nucleotides levels have a well-established role in inducing relaxation of contractile/quiescent smooth muscle cells on one hand and in inhibiting proliferation of synthetic/activated smooth muscle cells on the other hand[3]. MRP4/5 expression and function was analyzed in vitro and in vivo. We provide the first evidence that MRP4 acts as an independent endogenous regulator of cyclic nucleotide intra-cellular levels thus limiting the activation of mediated signal transduction. Our results then identify inhibition of MRP4 as a new way to enhance this signalling pathway.

RESULTS

MRP4 is Expressed in Coronary Artery Smooth Muscle Cells

We first analysed the expression of MRP4 and MRP5 in primary culture of human coronary artery smooth muscle cells (hCASMC). By RT-PCR, MRP4 and MRP5 mRNA were detected in hCASMC (FIG. 1a and FIG. 11a). Immunofluorescence analysis of MRP4 transfected hCASMC demonstrates a predominant plasma membrane location of the protein (FIG. 1b). By immunobloting, the expected 160-kDa MRP4 protein was detected in both total cell extracts and membrane preparations of smooth muscle cells whereas MRP5 protein was detected only in membranes enriched fractions (FIG. 11b). MRP5 was present in the endothelial layer of the coronary artery (FIG. 11c) We further investigated MRP4 location by separating smooth muscle cells proteins on a 5% to 40% discontinuous sucrose gradient. As shown in FIG. 1c, expression of the 160-kDa MRP4 protein was restricted to low-density fractions where the raft-associated protein caveolin1 was expressed.

Upregulation of MRP4 in Proliferating Arterial Smooth Muscle Cells

Expression of MRP4 and MRP5 was examined by western blotting in quiescent (0.1% supplement, S) and proliferating hCASMC stimulated by 5% S. An increase in MRP4 expression ($3.7 \pm 0.42$, $p=0.01$, FIG. 2a) but not in MRP5 (data not show) was detected in hCASMC culture. This overexpression correlated with the expression of cyclin D1, a marker of smooth muscle cell proliferation (FIG. 2a). To determine the significance of this increase in vivo, we analyzed the distribution of MRP4 in rat carotid arteries after balloon injury, a well-characterized model for smooth muscle cell proliferation. As shown in FIG. 2b, highly proliferative smooth muscle cells in the neo-intima displayed a strong MRP4 protein expression whereas MRP4 expression in the media was limited. We found a similar over-expression of MRP4 in proliferating hCASMC in atherosclerotic coronary arteries (FIG. 12). In both models, expression of MRP4 was correlated with that of NM-B, a marker of the switch from quiescent to proliferative phenotype of smooth muscle cell (FIG. 2b and FIG. 12). Overall, these data indicate that MRP4 is expressed at low level in quiescent arterial smooth muscle cells and is upregulated in response to proliferative stimuli.

Pharmacological Inhibition of MRP Inhibits Smooth Muscle Cell Proliferation

First, we checked the influence of cAMP and cGMP on hCASMC growth in our model. Treatment of hCASMC with the permeant 8-Bromo-cAMP (100 μM) or with the adenylate cyclase activator forskolin (5 μM) resulted in a significant inhibition of serum-induced proliferation (FIG. 3a, $p<0.001$). Similar results were observed using 8-Bromo-cGMP (200 μM) ($p=0.001$) or the NO donor SNP (1 mM) ($p<0.001$) confirming the already described anti-proliferative effect of cyclic nucleotides in vascular smooth muscle cells (FIG. 3a). To define the role of MRP4 and MRP5 during hCASMC proliferation, we then used pharmacological inhibitors of phosphodiesterases and MRPs (dipyridamole), of phosphodiesterases but not MRPs (IBMX) and of MRP4 and 5 (MK571) or of MRP4 (NBMPR) but not PDEs. We observed a dose-dependent inhibition of hCASMC proliferation when treated with each drug (FIG. 3b). In absence of inhibitors, stimulation by 5% S increased hCASMC proliferation by $240 \pm 15.8\%$ compared to 0.1% S. This increase was significantly reduced in a dose dependent way by MK571 and NBMPR to $153 \pm 11\%$ ($p<0.001$) and $140 \pm 15\%$ ($p<0.001$), respectively, at the maximal dose used of these inhibitors. Supplement mix-induced proliferation was also reduced by the PDE inhibitor IBMX (IBMX 100 µM: 170±12%; p<0.001 compared to 5% S) but to a lower extent than the one observed with MRPs inhibitors (p<0.04 compared to MK571 37.5 µM and p=0.007 compared to NBMPR 100 µM). On the other hand, no significant difference was observed with the global inhibitor dipyridamole compared to MK571 or NBMPR. These data indicate that MRP inhibition may inhibit hCASMC proliferation but with a stronger efficiency than PDE inhibition alone.

Inhibition of Arterial Smooth Muscle Cell Proliferation in vitro by MRP4 Small Interfering RNA To further investigate the role of MRP4 and MRP5 in hCASMC, we used RNA interference strategy to specifically silence MRP4 and/or MRP5 expression. Small interfering RNA against human MRP4 were designed and transfected in hCASMC providing, 72 hours after transfection, a decrease in MRP4 mRNA of 75±1% (p<0.001) (FIG. 13) and in protein level of 74±6.8% (p<0.001) (FIG. 4a) compared to scramble siRNA. Similar silencing efficiency was obtained for siRNA against human MRP5 (FIG. 13). Supplement mix-induced proliferation was significantly lower in hCASMC transfected with MRP4 siRNA than in those transfected with scramble siRNA (relative increase compared to 0.1% S: 183±27% and 313±35% respectively, p<0.001, FIG. 4b). Similar results were obtained by alternatively designed and validated MRP4 siRNA (data not shown). Furthermore, MRP4 siRNA was not associated with apoptosis in hCASMC (FIG. 15). On the other hand, we did not observe an influence of MRP5 siRNA on hCASMC proliferation (FIG. 4b), thus confirming that specific inhibition of MRP4 is sufficient to block hCASMC growth.

Adenoviral Vectors Expressing Specific MRP4 shRNA Prevent Neo-Intima Formation in vivo To assess the role of MRP4 in preventing vascular smooth muscle cell proliferation in vivo, we infected balloon-injured rat carotid arteries using an adenoviral vector expressing a short hairpin RNA designed against rat MRP4 mRNA (Ad-shMRP4). Firstly, the efficiency of Ad-shMRP4 to silence MRP4 expression was controlled in vitro on rat arterial smooth muscle cells. Seventy two hours after infection MRP4 mRNA and protein levels were lower than those observed in cells infected with the adenovirus expressing a luciferase shRNA (Ad-shLuc) (FIG. 14).

Two weeks after injury and infection with $10^{11}$ DNA particles of either Ad-shMRP4 or Ad shLuc, rats were sacrificed and a morphometric analysis of injured carotids was performed on hematoxylin/eosin stained cross-sections (FIG. 4c). The degree of restenosis was determined by measuring the intima and media thickness and calculating the intima/media (I/M) thickness ratio. I/M ratios from Ad-shMRP4-infected arteries were significantly lower than that of Ad-shLuc-infected carotids (p<0.03, FIG. 4d). To check for adenoviral infection, DNA from rat carotids was extracted in each sample and adenovirus expression was assayed by PCR with specific primers (FIG. 4e). These results show that decreasing MRP4 activity inhibits vascular smooth muscle cell proliferation in vitro and also balloon injury-induced neointima formation in vivo.

MRP4 Inhibition Increases Cellular Levels of cAMP and cGMP

Cells transfected with MRP4 siRNA displayed a significant change in cAMP and cGMP levels with a marked increase in the intra-cellular/extra-cellular ratio (289±12.5% and 230±5.5% respectively compared to scramble siRNA), indicating a reduction in cyclic nucleotide efflux from hCASMCs (FIGS. 5a and 5b).

To further analyse the influence of MRP4 inhibition on cAMP levels, hCASMCs transfected with either MRP4 or scramble siRNAs were infected with an adenovirus encoding Epac2-camps, a fluorescence resonance energy transfer (FRET)-based sensor for real-time cAMP imaging in living cells[13], and then challenged with increasing concentrations of forskolin. As shown in FIGS. 5c and d, application of forskolin at increasing concentrations elicited a cAMP rise reflected by the increase in the CFP/YFP ratio that indicates FRET changes between CFP and YFP. However, stimulation with lower doses of forskolin led to a greater change in FRET in hCASMCs transfected with MRP4 siRNA. As shown in FIG. 5e, MRP4 silencing results in a leftward shift in the concentration-response curve to forskolin without affecting the maximal effect of the drug. Hill fit of the data indicated that the dose of forskolin providing 50% of maximal cAMP formation was significantly lower in MRP4 siRNA transfected cells than in scramble siRNA transfected cells ($EC_{50}$: 3.0±0.6 µM versus 13.3±2.2 µM, p<0.001). This result confirms a faster cAMP availability in response to adenylate cyclase stimulation in cells under MRP4 inhibition.

MRP4 Inhibition Enhances the Effect of cAMP on hCASMC Proliferation by Activating the Protein Kinase A (PKA)

In keeping with the previous results, we observed that the dose-dependent anti-proliferative effect of forskolin was significantly enhanced in hCASMC transfected with MRP4 siRNA compared to scramble siRNA (FIG. 6a). In MRP4 siRNA transfected cells, a small amount of forskolin was sufficient to block hCASMC proliferation: inhibition constant (Ki) decreased from 0.79±0.56 µM in scramble siRNA to 0.11±0.01 µM in MRP4 siRNA transfected hCASMC. We did not observe a similar effect when using the cGMP activator SNP: Ki was 182±95 µM in scramble siRNA and 166±90 µM in MRP4 siRNA transfected cells (FIG. 6b).

These results indicate that MRP4 inhibition enhances the cAMP but not the cGMP effect on proliferation. We confirmed this by showing that the inhibitory effect of MRP4 siRNA on hCASMC proliferation was completely reversed by the inhibition of cAMP-dependent protein kinase A (PKA) via infection with Ad-PKI (a specific inhibitor of PKA) but not by the inhibition of cGMP-dependent protein kinase G (PKG) using the pharmacological inhibitor KT5823 (FIG. 6c). The effect of MRP4 pharmacological inhibitors MK571 and NMBPR on hCASMC proliferation was also reversed by the inhibition of PKA by infection with Ad-PKI but not by KT5823 (FIG. 6d).These results show that MRP4 inhibition enhances the cAMP effect on hCASMC proliferation by activating the PKA-dependent signalling pathway.

Because PKA regulates activity and phosphorylation of the cyclic AMP-responsive element binding protein (CREB) and because CREB is involved in inhibition of proliferation, we analyzed the level of phosphorylated CREB (pCREB) in proliferating hCASMC transfected with scramble siRNA or MRP4 siRNA. The level of pCREB was increased by 329±15% (p=0.003) with MRP4 inhibition whereas the level of total CREB was similar in both conditions (FIG. 6e). In addition, the activity of CREB was measured on cells transfected with a CRE-luciferase reporter gene. Luciferase activity was significantly higher in MRP4 siRNA compared to scramble siRNA transfected cells (553±25%, p<0.01, FIG. 6f). Thus we conclude that the anti-proliferative effect of MRP4 inhibition is related to the activation of the PKA/CREB pathway.

MRP4 and Pulmonary Hypertension

Immunofluorescence analysis of MRP4 expression in human pulmonary arteries, reveals an MRP4 expression in the media in a normal pulmonary artery. In pathological pulmonary arteries (from two patients with pulmonary hypertension), immunostaining shows that MRP4 is expressed in the media and in the neo-intima or in the hypertrophic media (see FIG. 8). Western blot analysis in cultured smooth muscle cells exposed for 72 h to 0% S or 5% S have shown a basal MRP4 expression in isolated smooth muscle cells from human pulmonary arteries which increases in proliferative conditions (see FIG. 9). MRP4 siRNA on cell inhibits human pulmonary artery smooth muscle cell proliferation (see FIG. 10).

Discussion

This study is the first to identify MRP4, an energy-dependent efflux pump, as a modulator of signal transduction mediated by cyclic nucleotides in the vascular system. Our results indicate that MRP4 acts as a negative regulator that limits the amplitude of cyclic nucleotide signalling in arterial smooth muscle cells. This effect is carried by the active transmembrane efflux of cyclic nucleotides out of the cells, thus limiting the activation of mediated signal transduction. In arterial smooth muscle cells, specific inhibition of MRP4 modifies the intra-cellular content of cyclic nucleotides and thus allows a dramatic enhancement of their anti-proliferative effect in vitro and in vivo. Inhibition of MRP4 thus is a new appealing approach for the treatment of vasculoproliferative disorders.

Until now, MRP4 has been mainly viewed as a physiological transporter mediating transmembrane export of endogenous or exogenous glutathion, glucuronate and sulfates conjugates[14]. For instance, MRP4 is expected to be a key actor of the urate elimination pathway[15]. MRP4 has been also reported as an active transporter of cyclic nucleotides[16-18]. Other studies have shown that MRP4 may mediate the efflux of antiviral[19,20] or anticancer[16] purine nucleotide analogs and MRP4 is also involved in storage and release of ADP in platelet-dense granules[21]. However, none of these previous studies had identified MRP4 as an upstream regulator of cyclic nucleotide-mediated signalling pathways. By using pharmacological MRP4 inhibitors or RNA interference-mediated knock-down of MRP4 in smooth muscle cells, we observed a significant increase in cAMP and cGMP intracellular levels with a concomitant decrease in extra-cellular levels under basal conditions. In line with these results, intracellular cAMP availability after stimulation by the adenylate cyclase activator, forskolin[22,23], was dramatically enhanced in cells lacking MRP4. These data were obtained without phosphodiesterase inhibition indicating that intracellular cyclic nucleotide content is determined by two independent mechanisms: efflux by MRP4 on one hand and catabolism by PDEs on the other hand (FIG. 7.).

MRP4 inhibition was associated with changes in both cAMP and cGMP levels. We observed however that inhibition of serum-induced proliferation was associated with an increase in protein kinase A activity because adding PKI (a specific inhibitor of protein kinase A) completely reversed the anti-proliferative effect of MRP4 inhibition whereas PKG blockade had no effect. The increase in the phosphorylation and activity of CREB, a nuclear target of the cAMP/PKA signalling pathway[24] is in line with an activation of the PKA pathway. Cell-type specific antiproliferative effects of cAMP and cGMP are well documented even if the involved mechanisms remain elusive. In particular, increased levels of cAMP are known to inhibit VSMC proliferation in vitro and to reduce formation of neointimal lesions after arterial injury in vivo[25-27]. This is in line with our results obtained in the same in vivo model which show a significant prevention of neointimal formation by using an adenoviral construct expressing a specific short hairpin RNA against MRP4. On the other hand, cGMP was also shown to inhibit VSMC proliferation in response to mitogens although with a lower efficiency than cAMP. The expression of a constitutively active PKG has been reported as a way to reduce neointima formation after balloon injury in rats[28]. We did not observe rescue of the MRP4 inhibitory effect after inhibition of protein kinase G, a key actor of cGMP-signalling pathway, raising concerns on whether MRP4 inhibition may selectively modulate the cAMP but not cGMP signalling pathway. However, previous observations suggested that cGMP can act through PKA[29]. Concordantly, it was recently shown that the anti-proliferative effect of cGMP may be linked to the inhibition of the S-phase kinase-associated protein-2 expression through activation of protein kinase A[30]. It is plausible that cGMP may not directly cross-activate PKA but rather increases cAMP levels by inhibiting the cAMP-hydrolyzing phosphodiesterase 3 as shown in proliferating vascular smooth muscle cells[31]. Moreover, intracellular effectors of cAMP and cGMP are compartmentalized in macromolecular complexes and MRP4 may be an additional partner of these complexes. In our experiments MRP4 was localized in caveolin-enriched membrane fractions. Caveola/lipid rafts are specialized membrane microdomains in which multimolecular complexes of signalling molecules are compartmentalized via interaction with caveolin-1[32]. MRP4 C-terminal protein sequence contains a consensus PDZ domain-binding motif[33] suggesting that MRP4 could interact tightly with other partners of membrane signalling complex. This indicates that MRP4 may act in specific subcellular domains and thus modulates an initial activation step of cyclic nucleotide-mediated signal transduction.

This study identified MRP4 as regulator of smooth muscle cell proliferation. MRP4 was weakly expressed in quiescent smooth muscle cells but its expression was induced under in vitro and in vivo conditions of proliferation. This may represent an endogenous positive feedback following cyclic nucleotide production but the factors regulating MRP4 expression are not known at the present. MRP4 thus represents an especially promising target as its expression correlates with a pathological response of smooth muscle cells. This indicates that MRP4 gains functional importance during the proliferative response of smooth muscle cells. This is supported by the absence of vascular defects in MRP4 knock-out mice[34]. In contrast with our results, previous studies reported expression of MRP5 in human smooth muscle cell[10,12] but they did not look for MRP4. In our hands, MRP5 was present at low level in vascular smooth muscle cells. However, it is unlikely that MRP5 will share similarities with MRP4 as we did not observe any changes in MRP5 expression in VSMC proliferative models, and efficient silencing of MRP5 had no effect on VSMC proliferation. We can, however, not exclude that other MRPs are involved in extrusion of cyclic nucleotides such as MRP8[35].

Our results point to MRP4 as an alternative or complementary mechanism in addition to the phosphodiesterases as modulators of intra-cellular homeostasis of cyclic nucleotides. One of the most intriguing results is that MRP4 inhibition was sufficient per se to modulate intra-cellular cyclic nucleotide levels and mediated signal transduction. We also observed in in vitro experiments that reduction of serum-induced proliferation was higher with MRP4 inhibitors than with IBMX, a common phosphodiesterase inhibitor. It is now well-known that phosphodiesterases are combined in a complex intracellular spatiotemporal organization[4] thus controlling specific subcellular pools of cyclic nucleotides. It has also been reported that some phosphodiesterases may translocate from cytoplasm to the nucleus in proliferating smooth muscle cells[36]. In contrast, MRP4 localization in caveolin-enriched fractions indicates that MRP4 may control in a closer way the level of neo-synthesized cAMP and cGMP[37,38]. Whether MRP4 may act as quencher of cyclic nucleotide production, whereas phosphodiesterases regulate more specific pools of cyclic nucleotides inside cells deserves further investigations (FIG. 7).

Finally, excessive smooth muscle cells proliferation is a fundamental process that contributes to the injury response in major arterial vessels. Such process is involved in numerous vascular disorders, including atherosclerosis, post-angioplasty restenosis, pulmonary arterial hypertension and vein-graft disease[39,40]. Several strategies have been used to modulate the cAMP and cGMP levels such as activation of the adenylyl/guanylate cyclases or the use of pharmacological inhibitors of phosphodiesterases. The expanding use of the PDE5A inhibitor sildenafil in the treatment of vasculoproliferative disorders, such as primary pulmonary hypertension, supports this approach. Sildenafil has interestingly been reported as an MRP4 inhibitor[41]. Whether its therapeutic efficacy could be linked to PDE5A or MRP4 inhibition (or both) remains now to be determined.

In conclusion, our results imply that MRP4 is an important and independent regulator of cAMP and cGMP signal transduction. Inhibition of MRP4 thus is a new therapeutic strategy to limit smooth muscle cell proliferation, an important mechanism involved in many pathological conditions.

MATERIALS AND METHODS

Reagents

MK571 was purchased from Alexis Biochemicals. NBMPR, Dipyridamole, IBMX, 8Br-cAMP, 8Br-cGMP, SNP, Forskolin were from Sigma-Aldrich (France). The protein kinase inhibitor KT5823 was purchased from Calbiochem. The adenovirus PKI (Ad-PKI) was provided by Dr Hazel Lum (University of Illinois, Chicago)[42].

All media and sera for culture of human VSMC were purchased from PromoCell (PromoCell GmbH, Heidelberg, Germany); antibiotics were purchased from Invitrogen (Cergy Pontoise, France).

Human Samples and Culture of Human Vascular Smooth Muscle ells

Fragments of inter ventricular coronary artery were dissected from explanted hearts. After removal, the artery segments were immediately immersed in physiological saline solution, placed at 4° C. and used within few hours. Human coronary artery smooth muscle cells (hCASMC) were isolated from the media layer by enzymatic digestion. After dissection, the fragments of media were incubated in smooth muscle cells basal medium 2 (SMCBM2, PromoCell) with collagenase (CLS2, 50 U/mL, Worthington) and pancreatic elastase (0.25 mg/mL, Sigma) for 4-6 hours at 37° C. After periods of 30 minutes, the suspension was centrifuged at 1000 rpm for 3 minutes, and the cells were collected and placed in SMCBM2 +20% SupplementMix (S) (PromoCell). The cells obtained in the first 20-minutes period were discarded. Those obtained in the other cycles were pooled and cultured in SMCBM2 containing 5% of S and antibiotics at 37° C. in 5% of $CO_2$. Cells were studied between passages 2 to 6.

Injury of the Rat Carotid Artery

Animals were treated in accordance with institutional guidelines. The left external carotid artery from adult male wistar rats (CERJ, France) weighing 350 to 400 g was injured as previously described[43]. Two weeks after surgery carotids were collected. Intima-to-media thickness ratio was measured from hematoxylin-and eosin-stained cross-sections with a computer-based software (Lucia, Nikon). DNA from rat injured carotids was extracted using standard procedures (Puregene® DNA Purification Kit from Gentra (US)). Adenovirus expression was then assayed by PCR using a sense primer targeting the inserted expression cassette (5'-TCT-TGTGGAAAGGACGAGGA-3' (SEQ ID NO:10)) and an antisense primer in the adenoviral DNA (5'-ATCAAAC-GAGTTGGTGCTCA-3' (SEQ ID NO:11)).

Quantitative Real-Time PCR

Total RNA was prepared using RNeasy Mini Kit (Invitrogen) and 1 μg was reverse-transcribed using a standard protocol. One tenth of the resulting cDNA was amplified by 35 cycles of 30 s at 94° C., 30 s at Tm (60° C. for MRP4, MRP5 and RPL32) and 30 s at 72° C., followed by a final amplification at 72° C. for 10 min using 1 unit of BIOTAQ DNA Polymerase (Bioline) and 200 pmol each of the following primers:

```
human MRP4 sense primer,:
                                        (SEQ ID NO: 1)
5'-TGGTGCAGAAGGGGACTTAC-3'
and antisense primer,
                                        (SEQ ID NO: 2)
5'-GCTCTCCAGAGCACCATCTT-3';

human MRP5 sense primer
                                        (SEQ ID NO: 3)
5'-CTGGGCTTTTTTCCTGTATGA-3'
and antisense primer,
                                        (SEQ ID NO: 4)
5'-TCTTGCCACAGTCTCTCTAGTCTT-3';

human RPL32 sense primer,
                                        (SEQ ID NO: 5)
5'-GCCCAAGATCGTCAAAAAGA-3'
and antisense primer,
                                        (SEQ ID NO: 6)
5'-GTCAATGCCTCTGGGTTT-3', beta-actin sense primer
                                        (SEQ ID NO: 12)
5'-CACCTTCTACAATGAGCTGTGCTTGC-3'
and antisense primer
                                        (SEQ ID NO: 13)
5'-TGATCCACATCTGCTGGAAGGTGGACGTGTGGC-3'.
```

Gene specific primers were used to amplify mRNA by qPCR on a Mx4000 apparatus (Stratagene) using the Qiagen SYBR Green master mix. The specificity of each primer set was monitored by analysis of the dissociation curve. A sample volume of 25 μl was used for each assay, which contained a 1× final concentration of SYBR green PCR master mix, 400 nM gene specific primers, and 5 μl template.

Sucrose Gradient Separation and SDS-PAGE:

Proteins were isolated by scraping the cells in 2 ml TNE solution (in mM) (20 Tris; 150 NaCl; 1 EDTA, pH 7.4) in which a cocktail of protease inhibitors (Sigma) was added and then homogenized on ice with a glass potter. Triton X-100 was then added to the total protein fraction with a final concentration of 1% in order to solubilize proteins localized in the bulk plasma membrane. Note that all steps of the protein extraction were performed at 4° C., at this temperature lipid rafts are insoluble in 1% Triton X-100. After 30 minutes incubation on ice, the protein concentration was determined using a Bio-rad protein assay (Biorad Laboratories). Two ml of 80% sucrose solution wer placed in a SW41 centrifuge tube (Beckman), 2 ml of total extract were placed on the sucrose solution and the preparation was mixed. Four ml of 35% sucrose were gently poured onto the mixture, followed by 4 ml of 5% sucrose. The gradient was then centrifuged for 18 hours at 40000 rpm and 4° C., without brake. Fractions of 1 ml were collected from the top to the bottom of the gradient and kept at −80° C. Each sample fraction was sonicated, 60 µl were loaded onto a 12.5% polyacrylamide-SDS gel and analyzed by western-blot.

Western Blot Analysis and Immunofluorescence

Total cell lysates were prepared according to standard protocol (Upstate Biotechnology). Membrane proteins were isolated by scraping the cells in buffer A (5 mmol/L Tris/HCl, 250 mmol/L sucrose, and 0.1 mmol/L ethylenediaminetetraacetic acid supplemented with protease inhibitors cocktail (Sigma). The lysate was centrifuged at 10000 g for 10 min at 4° C. and the supernatant further centrifuged at 100000 g for 1 h at 4° C. The resulting pellet was resuspended in buffer A. Proteins (50 µg) were separated by SDS 12% PAGE, blotted on Hybond-C membrane (Amersham Biosciences) and incubated with various antibodies. The anti-MRP4 antibody was previously described[17]. Other antibodies were: anti-MRP5 antibody (1:250; Santa-Cruz Biotechnology), anti-Caveolin1 (1:5000, Abcam), anti-cyclinD1 (1:500, BD Biosciences), anti-PP2B (calcineurin) (1:250; BD Biosciences), anti-CREB (1:1000; Upstate Biotechnology), anti-phosphorylated CREB (1:1000; Upstate Biotechnology). Immunoreactive proteins were visualized using an ECL® (enhanced chemiluminescence) detection system (Amersham Biosciences). Optical Density was quantified using ImageJ software (National Institutes of Health, Bethesda, Md.). For immunofluorescence, proteins were incubated with the anti-MRP4 antibody or the anti-NM-B (1:3000; Abcam) visualized by using secondary antibodies directly conjugated either to Alexa-546 or to Alexa-488 (Invitrogen).

RNA Interference

Silencing RNA was specifically designed against human MRP4. The sequence for siRNA was designed to target the several MRP4 splicing variants (NM_005845, BC041560, AY081219, AF541977, AY133680, AY133679, AY133678). The sense sequence is 5'-CAGUGUUCUUACACUUC-CUTT-3' (SEQ ID NO:7) and anti-sense: 5'-AGGAAGU-GUAAGAACACUGTT-3' (SEQ ID NO:8). For the second MRP4 siRNA, the targeted sequence was 5'-CAAATGTG-GATCCGAGAA-3'. siRNA against human MRP5 was purchased from Ambion (Cat:AM16810). A non silencing siRNA without homology for mammalian genes (All Stars negative Control, Qiagen) was used as negative control (scramble siRNA).

Cells were transfected with siRNA (50 nM) in serum free medium over a period of 6 h, the medium was then replaced with serum-containing medium for a further period of 66 h. Transfection was performed using Lipofectamine 2000 (Invitrogen) or electroporation using amaxa® Nucleofector technology according to manufacturer's instructions.

Construction of Ad-shRNA shRNA was specifically designed against rat MRP4. This shRNA will target also human MRP4. The shRNA was annealed and ligated via BamHI/EcoRI into pSIREN vector using Knockout RNAi Systems (Clontech). The recombinant pSIREN was then transformed in *E. coli* cells using FusionBlue Competent Cells (Clontech). The fragment was then cut out with PI-Sce I/I-Ceu I and inserted into Adeno-X Viral DNA via PI-Sce I/I-Ceu I using Adeno-X Expression System 1 (Clontech). The resulting Adenovirus was transfected into HEK293 cells and propagated generating the AdVs termed Ad-shMRP4 (FIG. 14) and Ad-shLuc.

For testing the efficiency of the adenoviral construct, VSMC were isolated from the media of the thoracic aorta from male Wistar rats and cultured as previously described[44].

Bromodeoxyuridine Incorporation in Smooth Muscle Cells

Human smooth muscle cells were cultured in 96-wells tissue culture plates for 3 days in Smooth Muscle Cell Basal Medium 2 supplemented with 5% S. Medium containing 0.1% S was used for the growth arrest control. Cells were incubated with pharmacological agents or siRNA for 72 h in medium containing 5% S. BrdU was added for the last 16 hours. The cell culture plates were washed, and a colorimetric BrdU cell proliferation assay was performed according to the manufacturer's instructions (Roche).

Cyclic GMP and AMP Assays

Cyclic GMP and AMP were measured in cell culture supernates and in cell lysates in hCASMC transfected for 72 h either with the scramble siRNA or the MRP4 siRNA by specific competitive enzyme immunoassay as described by the manufacturer (R&D systems).

Transient Transfection and Reporter Gene Assay

Cells were co-transfected with the siRNA (50 nM) and the the CRE-luciferase reporter gene plasmid (Stratagene) by electroporation using amaxa® Nucleofector technology according to manufacturer's instructions. After, a period of 6 h, the medium was replaced with supplement containing medium. Cells were grown in the presence of 5% S for 66 h. The results are means for three independent experiments performed in triplicate. The luciferase activity was measured by using "the luciferase assay kit" (Promega). It was expressed as percent of control in relative luciferase units.

Fluorescence Resonance Energy Tranfer Imaging of cAMP hCASMCs were transfected with scramble siRNA or the siRNA against MRP4 (each at 50 nM) in supplement-free medium over a period of 6 h, before the medium was replaced with supplement-containing medium. 24 h after the transfection, cells were infected with an adenovirus encoding the FRET-based cAMP sensor Epac2-camps. This FRET-based cAMP sensor contains a single cAMP binding domain of Epac2 fused to YFP and CFP fluorescent proteins. Upon addition of forskolin, increasing intra-cellular cAMP concentrations lead to a reversible conformational change of Epac2-camps which results in a decrease of FRET between CFP and YFP, leading to an increase in the CFP/YFP ratio[13]. Imaging experiments were performed at 72 h and at room temperature. Cells were maintained in a $K^+$-Ringer solution containing (in mmol/L): NaCl 121.6, KCl 5.4, $MgCl_2$ 1.8; $CaCl_2$ 1.8; $NaHCO_3$ 4, $NaH_2PO_4$ 0.8, D-glucose 5, sodium pyruvate 5, HEPES 10, adjusted to pH 7.4. Images were captured every 5 s using the 40× oil immersion objective of a Nikon TE 300 inverted microscope connected to a software-controlled (Metafluor, Molecular Devices, Sunnyvale, Calif., USA) cooled charge coupled (CCD) camera (Sensicam PE; PCO, Kelheim, Germany). CFP was excited during 150-300 ms by a Xenon lamp (100 W, Nikon, Champigny-sur-Marne, France) using a 440/20BP filter and a 455LP dichroic mirror. Dual emission imaging of CFP and YFP was performed using an Optosplit II emission splitter (Cairn Research, Faversham, UK) equipped with a 495LP dichroic mirror and BP filters 470/30 and 535/30, respectively. Average fluorescence intensity was measured in a region of interest comprising the entire cell. Background was subtracted and YFP intensity was corrected for CFP spillover into the 535 nm channel before calculating the CFP/YFP ratio. Ratio images were obtained with ImageJ software (National Institute of Health).

Isolation of Full-Length Human MRP4

Total RNA was isolated from human tissue using TRIzol Reagent (Invitrogen) and 1 pg was reverse-transcribed using a standard protocol. For amplification of MRP4 cDNA primers were designed on the basis of the published human sequence (nucleotides 1 to 3979, GenBank accession number (AF071202)). One tenth of the resulting cDNA was amplified by 35 cycles of 30 s at 94° C., 30 s at 60° C. and 30 s at 72° C., followed by a final amplification at 72° C. for 10 min using 1 unit of BIOTAQ DNA Polymerase (Bioline) and 200 pmol each of the following primers. The resulting fragment was cloned into the pIRES-GFP plasmid.

Statistical Analysis

All quantitative data are presented as means ±SD. Statistical analysis were performed using the Prism software package (GraphPad v3). One-way analysis of variance (ANOVA) was used to compare each parameter. Post hoc t-test comparisons were performed to identify which group differences accounted for the significant overall ANOVA. The concentration-response curve for the effect of forskolin on the normalized CFP/YFP ratio (R) was fitted to the Hill equation: $R=E_{max}/(1+EC_{50}/[forsk]^n)$, where $EC_{50}$ is the drug concentration required to produce half-maximal stimulation, $E_{max}$ is the maximal effect and n is the Hill coefficient. Differences were considered significant when $P<0.05$.

REFERENCES

Throughout this application, various references describe the state of the art to which this invention pertains. The disclosures of these references are hereby incorporated by reference into the present disclosure.

Assender J W, Southgate K M, Hallett M B, Newby A C. Inhibition of proliferation, but not of Ca2+ mobilization, by cyclic AMP and GMP in rabbit aortic smooth-muscle cells, Biochem J. 1992 Dec. 1; 288 (Pt 2):527-32.

Boerth N J, Dey N B, Cornwell T L, Lincoln T M. Cyclic GMP-dependent protein kinase regulates vascular smooth muscle cell phenotype. J Vasc Res. 1997 July-August; 34(4): 245-59.

Brummelkamp T R, Bernards R, Agami R. A system for stable expression of short interfering RNAs in mammalian cells. Science. 2002 Apr. 19; 296(5567):550-3.

Chen Z S, Lee K, Kruh G D. Transport of cyclic nucleotides and estradiol 17-beta-D-glucuronide by multidrug resistance protein 4. Resistance to 6-mercaptopurine and 6-thioguanine. J Biol Chem. 2001 Sep. 7; 276(36):33747-54. Epub 2001 Jul. 10.

Choi V W, Samulski R J, McCarty D M. Effects of adeno-associated virus DNA hairpin structure on recombination. J Virol. 2005 June; 79(11):6801-7.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cote R J, Morrissey D M, Houghton A N, Beattie E J Jr, Oettgen H F, Old L J. Generation of human monoclonal antibodies reactive with cellular antigens. Proc Natl Acad Sci U S A. 1983 April; 80(7):2026-30.

Desgranges P, Caruelle J P, Carpentier G, Barritault D, Tardieu M. Beneficial use of fibroblast growth factor 2 and RGTA, a new family of heparan mimics, for endothelialization of PET prostheses. J Biomed Mater Res. 2001; 58(1):1-9.

Dzau V J, Braun-Dullaeus R C, Sedding D G. Vascular proliferation and atherosclerosis: new perspectives and therapeutic strategies. Nat Med. 2002 November; 8(11):1249-56.

Elbashir Sfvl, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Hannon G J. RNA interference. Nature. 2002 Jul. 11; 418 (6894):244-51.

Jayasena S. D. (1999) Aptamers: an emerging class of molecules that rival antibodies in diagnostics. Clin Chem. 45(9):1628-50.

Jedlitschky G, Burchell B, Keppler D The multidrug resistance protein 5 functions as an ATP-dependent export pump for cyclic nucleotides. J Biol Chem. 2000 Sep. 29; 275(39): 30069-74.

Kohler G, Milstein C. Continuous cultures of fused cells secreting antibody of predefined specificity. Nature. 1975 Aug. 7; 256(5517):495-7.

Kriegler, A Laboratory Manual," W.H. Freeman C.O., New York, 1990.

McDonald L J, Murad F. Nitric oxide and cyclic GMP signaling. Proc Soc Exp Biol Med. 1996 January; 211(1):1-6.

McManus M T, Sharp P A. Gene silencing in mammals by small interfering RNAs. Nat Rev Genet. 2002 October; 3(10): 737-47.

Mitani A, Nakahara T, Sakamoto K, Ishii K. Expression of multidrug resistance protein 4 and 5 in the porcine coronary and pulmonary arteries. Eur J Pharmacol. 2003 Apr. 11; 466 (1-2):223-4.

Murry, "Methods in Molecular Biology," vol. 7, Humana Press, Inc., Cliffton, N.J., 1991.

Novak K. Cardiovascular disease increasing in developing countries. Nat Med. 1998 September; 4(9):989-90.

Rybalkin S D, Yan C, Bornfeldt K E, Beavo J A. Cyclic GMP phosphodiesterases and regulation of smooth muscle function. Circ Res. 2003 Aug. 22; 93(4):280-91. Review.

Sinnaeve P, Chiche J D, Gillijns H, Van Pelt N, Wirthlin D, Van De Werf F, Collen D, Bloch K D, Janssens S. Overexpression of a constitutively active protein kinase G mutant reduces neointima formation and in-stent restenosis. Circulation. 2002 Jun. 18; 105(24):2911-6.

Sunahara R K, Dessauer C W, Gilman A G. Complexity and diversity of mammalian adenylyl cyclases. Annu Rev Pharmacol Toxicol. 1996; 36:461-80.

Tuerk C. and Gold L. (1990) Systematic evolution of ligands by exponential enrichment: RNA ligands to bacteriophage T4 DNA polymerase. Science. 3;249(4968):505-10.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Wu Z, Asokan A, Samulski R J. Adeno-associated virus serotypes: vector toolkit for human gene therapy. Mol Ther. 2006 September; 14(3):316-27. Epub 2006 Jul. 7.

1. Kaupp, U. B. & Seifert, R. Cyclic nucleotide-gated ion channels. *Physiological reviews* 82, 769-824 (2002).
2. Rehmann, H., Wittinghofer, A. & Bos, J. L. Capturing cyclic nucleotides in action: snapshots from crystallographic studies. *Nature reviews* 8, 63-73 (2007).
3. Rybalkin, S. D., Yan, C., Bornfeldt, K. E. & Beavo, J. A. Cyclic GMP phosphodiesterases and regulation of smooth muscle function. *Circulation research* 93, 280-291 (2003).
4. Fischmeister, R., et al. Compartmentation of cyclic nucleotide signaling in the heart: the role of cyclic nucleotide phosphodiesterases. *Circulation research* 99, 816-828 (2006).
5. Takimoto, E., et al. Chronic inhibition of cyclic GMP phosphodiesterase 5A prevents and reverses cardiac hypertrophy. *Nature medicine* 11, 214-222 (2005).

6. Humbert, M., Sitbon, O. & Simonneau, G. Treatment of pulmonary arterial hypertension. *The New England journal of medicine* 351, 1425-1436 (2004).
7. Sampath, J., et al. Role of MRP4 and MRP5 in biology and chemotherapy. *AAPS pharmSci* 4, E14 (2002).
8. Borst, P., de Wolf, C. & van de Wetering, K. Multidrug resistance-associated proteins 3, 4, and 5. *Pflugers Arch* 453, 661-673 (2007).
9. Ritter, C. A., et al. Cellular export of drugs and signaling molecules by the ATP-binding cassette transporters MRP4 (ABCC4) and MRP5 (ABCC5). *Drug metabolism reviews* 37, 253-278 (2005).
10. Dazert, P., et al. Expression and localization of the multidrug resistance protein 5 (MRP5/ABCC5), a cellular export pump for cyclic nucleotides, in human heart. *The American journal of pathology* 163, 1567-1577 (2003).
11. Mitani, A., Nakahara, T., Sakamoto, K. & Ishii, K. Expression of multidrug resistance protein 4 and 5 in the porcine coronary and pulmonary arteries. *European journal of pharmacology* 466, 223-224 (2003).
12. Nies, A. T., Spring, H., Thon, W. F., Keppler, D. & Jedlitschky, G. Immunolocalization of multidrug resistance protein 5 in the human genitourinary system. *The Journal of urology* 167, 2271-2275 (2002).
13. Nikolaev, V. O., Bunemann, M., Hein, L., Hannawacker, A. & Lohse, M. J. Novel single chain cAMP sensors for receptor-induced signal propagation. *The Journal of biological chemistry* 279, 37215-37218 (2004).
14. Deeley, R. G., Westlake, C. & Cole, S. P. Transmembrane transport of endo- and xenobiotics by mammalian ATP-binding cassette multidrug resistance proteins. *Physiological reviews* 86, 849-899 (2006).
15. Van Aubel, R. A., Smeets, P. H., van den Heuvel, J. J. & Russel, F. G. Human organic anion transporter MRP4 (ABCC4) is an efflux pump for the purine end metabolite urate with multiple allosteric substrate binding sites. *American journal of physiology* 288, F327-333 (2005).
16. Chen, Z. S., Lee, K. & Kruh, G. D. Transport of cyclic nucleotides and estradiol 17-beta-D-glucuronide by multidrug resistance protein 4. Resistance to 6-mercaptopurine and 6-thioguanine. *The Journal of biological chemistry* 276, 33747-33754 (2001).
17. van Aubel, R. A., Smeets, P. H., Peters, J. G., Bindels, R. J. & Russel, F. G. The MRP4/ABCC4 gene encodes a novel apical organic anion transporter in human kidney proximal tubules: putative efflux pump for urinary cAMP and cGMP. *J Am Soc Nephrol* 13, 595-603 (2002).
18. Wielinga, P.R., et al. Characterization of the MRP4- and MRP5-mediated transport of cyclic nucleotides from intact cells. *The Journal of biological chemistry* 278, 17664-17671 (2003).
19. Schuetz, J. D., et al. MRP4: A previously unidentified factor in resistance to nucleoside-based antiviral drugs. *Nature medicine* 5, 1048-1051 (1999).
20. lmaoka, T., et al. Functional involvement of multidrug resistance-associated protein 4 (MRP4/ABCC4) in the renal elimination of the antiviral drugs adefovir and tenofovir. *Molecular pharmacology* 71, 619-627 (2007).
21. Jedlitschky, G., et al. The nucleotide transporter MRP4 (ABCC4) is highly expressed in human platelets and present in dense granules, indicating a role in mediator storage. *Blood* 104, 3603-3610 (2004).
22. McDonald, L. J. & Murad, F. Nitric oxide and cyclic GMP signaling. *Proceedings of the Society for Experimental Biology and Medicine. Society for Experimental Biology and Medicine* (New York, N.Y. 211, 1-6 (1996).
23. Sunahara, R. K., Dessauer, C. W. & Gilman, A. G. Complexity and diversity of mammalian adenylyl cyclases. *Annual review of pharmacology and toxicology* 36, 461-480 (1996).
24. Klemm, D. J., et al. cAMP response element-binding protein content is a molecular determinant of smooth muscle cell proliferation and migration. *The Journal of biological chemistry* 276, 46132-46141 (2001).
25. Indolfi, C., et al. Activation of cAMP-PKA signaling in vivo inhibits smooth muscle cell proliferation induced by vascular injury. *Nature medicine* 3, 775-779 (1997).
26. Assender, J. W., Southgate, K. M., Hallett, M. B. & Newby, A. C. Inhibition of proliferation, but not of Ca2+ mobilization, by cyclic AMP and GMP in rabbit aortic smooth-muscle cells. *The Biochemical journal* 288 (Pt 2), 527-532 (1992).
27. Southgate, K. & Newby, A. C. Serum-induced proliferation of rabbit aortic smooth muscle cells from the contractile state is inhibited by 8-Br-cAMP but not 8-Br-cGMP. *Atherosclerosis* 82, 113-123 (1990).
28. Sinnaeve, P., et al. Overexpression of a constitutively active protein kinase G mutant reduces neointima formation and in-stent restenosis. *Circulation* 105, 2911-2916 (2002).
29. Cornwell, T. L., Arnold, E., Boerth, N. J. & Lincoln, T. M. Inhibition of smooth muscle cell growth by nitric oxide and activation of cAMP-dependent protein kinase by cGMP. *The American journal of physiology* 267, C1405-1413 (1994).
30. Wu, Y. J., Bond, M., Sala-Newby, G. B. & Newby, A. C. Altered S-phase kinase-associated protein-2 levels are a major mediator of cyclic nucleotide-induced inhibition of vascular smooth muscle cell proliferation. *Circulation research* 98, 1141-1150 (2006).
31. Aizawa, T., et al. Role of phosphodiesterase 3 in NO/cGMP-mediated antiinflammatory effects in vascular smooth muscle cells. *Circulation research* 93, 406-413 (2003).
32. Gratton, J. P., Bernatchez, P. & Sessa, W. C. Caveolae and caveolins in the cardiovascular system. *Circulation research* 94, 1408-1417 (2004).
33. Russel, F. G., Masereeuw, R. & van Aubel, R. A. Molecular aspects of renal anionic drug transport. *Annual review of physiology* 64, 563-594 (2002).
34. Leggas, M., et al. Mrp4 confers resistance to topotecan and protects the brain from chemotherapy. *Molecular and cellular biology* 24, 7612-7621 (2004).
35. Guo, Y., et al. MRP8, ATP-binding cassette C11 (ABCC11), is a cyclic nucleotide efflux pump and a resistance factor for fluoropyrimidines 2,3'-dideoxycytidine and 9'-(2'-phosphonylmethoxyethyl)adenine. *The Journal of biological chemistry* 278, 29509-29514 (2003).
36. Nagel, D. J., et al. Role of nuclear Ca2+/calmodulin-stimulated phosphodiesterase 1A in vascular smooth muscle cell growth and survival. *Circulation research* 98, 777-784 (2006).
37. Ostrom, R. S., et al. Localization of adenylyl cyclase isoforms and G protein-coupled receptors in vascular smooth muscle cells: expression in caveolin-rich and non-caveolin domains. *Molecular pharmacology* 62, 983-992 (2002).
38. Linder, A. E., McCluskey, L. P., Cole, K. R., 3rd, Lanning, K. M. & Webb, R. C. Dynamic association of nitric oxide downstream signaling molecules with endothelial caveolin-1 in rat aorta. *The Journal of pharmacology and experimental therapeutics* 314, 9-15 (2005).

39. Dzau, V. J., Braun-Dullaeus, R. C. & Sedding, D. G. Vascular proliferation and atherosclerosis: new perspectives and therapeutic strategies. *Nature medicine* 8, 1249-1256 (2002).
40. Novak, K. Cardiovascular disease increasing in developing countries. *Nature medicine* 4, 989-990 (1998).
41. Reid, G., et al. Characterization of the transport of nucleoside analog drugs by the human multidrug resistance proteins MRP4 and MRP5. *Molecular pharmacology* 63, 1094-1103 (2003).
42. Lum, H., et al. Expression of PKA inhibitor (PKI) gene abolishes cAMP-mediated protection to endothelial barrier dysfunction. *The American journal of physiology* 277, C580-588 (1999).
43. Lipskaia, L., et al. Sarco/endoplasmic reticulum Ca2+-ATPase gene transfer reduces vascular smooth muscle cell proliferation and neointima formation in the rat. *Circulation research* 97, 488-495 (2005).
44. Vallot, O., et al. Intracellular Ca(2+) handling in vascular smooth muscle cells is affected by proliferation. *Arteriosclerosis, thrombosis, and vascular biology* 20, 1225-1235 (2000).

The invention claimed is:

1. A method for the treatment of a vascular disorder characterized by excessive smooth muscle cell proliferation in a subject comprising administering to the subject a therapeutically effective amount of a pharmaceutical composition comprising a small molecule inhibitor of MRP4 or an nucleic acid-based inhibitor molecule targeted to MRP4 wherein administration of said inhibitor produces a decrease in smooth muscle cell proliferation or inhibits neo-intima formation, wherein said vascular disorder is selected from the group consisting of atherosclerosis, post-angioplasty restenosis, pulmonary arterial hypertension and vein-graft disease.

2. A method for inhibiting the proliferation or growth of smooth muscle cells in a subject comprising administering to the subject a therapeutically effective amount of a pharmaceutical composition comprising a small molecule inhibitor of MRP4 or a nucleic acid-based inhibitor molecule targeted to MRP4 wherein administration of said inhibitor produces a decrease in smooth muscle cell proliferation or inhibits neo-intima formation.

3. The method of claim 1, wherein the inhibitor is an inhibitor of MRP4 expression.

4. The method of claim 3, wherein said nucleic acid based inhibitor of MRP4 expression is selected from the group consisting of antisense RNA or DNA molecules, small inhibitory RNAs (siRNAs), short hairpin RNA and ribozymes.

5. The method of claim 4, wherein said inhibitor of MRP4 expression is a short hairpin RNA comprising the sequence as set forth in SEQ ID NO: 9.

6. A method of inhibition of proliferation or growth of arterial smooth muscle cells in a subject comprising administering to the subject a therapeutically effective amount of a pharmaceutical composition comprising an siRNA or shRNA molecule targeted to MRP4 wherein administration of said composition produces a decrease in arterial smooth muscle cell proliferation or inhibits neo-intima formation in said subject.

7. The method of claim 6 wherein shRNA is a short hairpin RNA comprising the sequence as set forth in SEQ ID NO: 9.

8. The method of claim 1, wherein said vascular disorder is pulmonary hypertension.

9. The method of claim 8 further comprising administering to said subject a composition comprising one or more Phosphodiesterase (PDE) inhibitors selected from the group consisting of PDE3 inhibitors, PDE4 inhibitors, PDE5 inhibitors and mixtures thereof.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
tggtgcagaa ggggacttac                                                    20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
gctctccaga gcaccatctt                                                    20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
ctgggctttt ttcctgtatg a                                                  21

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
tcttgccaca gtctctctag tctt                                               24

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gcccaagatc gtcaaaaaga                                                    20
```

```
<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
gtcaatgcct ctgggttt                                                     18

<210> SEQ ID NO 7
<211> LENGTH: 21
<212> TYPE: DNA
<213> ORGANISM: Artificial
<220> FEATURE:
<223> OTHER INFORMATION: siRNA

<400> SEQUENCE: 7
caguguucuu acacuuccut t                                                 21

<210> SEQ ID NO 8
<211> LENGTH: 21
<212> TYPE: DNA
<213> ORGANISM: Artificial
<220> FEATURE:
<223> OTHER INFORMATION: siRNA

<400> SEQUENCE: 8
aggaagugua agaacacugt t                                                 21

<210> SEQ ID NO 9
<211> LENGTH: 19
<212> TYPE: DNA
<213> ORGANISM: Artificial
<220> FEATURE:
<223> OTHER INFORMATION: shRNA

<400> SEQUENCE: 9
gcaaatgtgg atccgagaa                                                    19

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tcttgtggaa aggacgagga                                                   20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
atcaaacgag ttggtgctca                                                   20

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12
```

```
caccttctac aatgagctgt gcttgc                                        26

<210> SEQ ID NO 13
<211> LENGTH: 33
<212> TYPE: DNA
<213> ORGANISM: Artificial
<220> FEATURE:
<223> OTHER INFORMATION: primer

<400> SEQUENCE: 13
tgatccacat ctgctggaag gtggacgtgt ggc                                33

<210> SEQ ID NO 14
<211> LENGTH: 64
<212> TYPE: DNA
<213> ORGANISM: Artificial
<220> FEATURE:
<223> OTHER INFORMATION: shRNA

<400> SEQUENCE: 14
atccgcaaat gtggatccga gaattcaaga gattctcgga tccacatttg cttttttacg   60
cgtg                                                                64

<210> SEQ ID NO 15
<211> LENGTH: 65
<212> TYPE: DNA
<213> ORGANISM: Artificial
<220> FEATURE:
<223> OTHER INFORMATION: shRNA

<400> SEQUENCE: 15
gcgtttacac ctaggctctt aagttctcta agagcctagg tgtaaacgaa aaatgcgca    60 cttaa                                                               65
```